US005687504A

United States Patent [19]
Carlson et al.

[11] Patent Number: 5,687,504
[45] Date of Patent: *Nov. 18, 1997

[54] MANUFACTURED SEED COTYLEDON RESTRAINT

[75] Inventors: William C. Carlson, Olympia; Jeffrey E. Hartle, Federal Way, both of Wash.; Barbara K. Bower, Hot Springs, Ark.

[73] Assignee: Weyerhaeuser Company, Tacoma, Wash.

[*] Notice: The term of this patent shall not extend beyond the expiration date of Pat. Nos. 5,427,593 and 5,564,224.

[21] Appl. No.: 414,021

[22] Filed: Mar. 31, 1995

Related U.S. Application Data

[63] Continuation of Ser. No. 781,773, Oct. 23, 1991, Pat. No. 5,427,593, which is a continuation-in-part of Ser. No. 604,656, Oct. 26, 1990, Pat. No. 5,236,469.

[51] Int. Cl.$^6$ .................. A01C 1/06; A01G 1/00; A01H 5/00
[52] U.S. Cl. .................. 47/57.6; 47/58; 47/DIG. 9; 47/DIG. 11; 800/200
[58] Field of Search ................ 47/57.6, 58, DIG. 9, 47/DIG. 11; 800/200; 435/177–180, 214, 240.4, 240.45, 420; 514/756, 747, 786, 832, 937

[56] References Cited

U.S. PATENT DOCUMENTS

| | | | |
|---|---|---|---|
| 3,545,129 | 12/1970 | Schreiber et al. | 47/57.6 |
| 3,688,437 | 9/1972 | Hamrin | 47/57.6 |
| 3,734,987 | 5/1973 | Hamrin | 47/57.6 |
| 3,850,753 | 11/1974 | Chibata et al. | 435/248 |
| 4,166,006 | 8/1979 | Hertl et al. | 435/244 |
| 4,252,827 | 2/1981 | Yokoyama et al. | 514/776 |
| 4,465,017 | 8/1984 | Simmons | 118/418 |
| 4,562,663 | 1/1986 | Redenbaugh | 47/58 |
| 4,583,320 | 4/1986 | Redenbaugh | 47/57.6 |
| 4,615,141 | 10/1986 | Janick et al. | 47/57.6 |
| 4,665,648 | 5/1987 | Branco et al. | 47/57.6 |
| 4,715,143 | 12/1987 | Redenbaugh et al. | 47/57.6 |
| 4,753,035 | 6/1988 | Ryan et al. | 47/57.6 |
| 4,769,945 | 9/1988 | Motoyama et al. | 47/57.6 |
| 4,777,762 | 10/1988 | Redenbaugh et al. | 47/57.6 |
| 4,779,376 | 10/1988 | Redenbaugh | 47/57.6 |
| 4,780,987 | 11/1988 | Nelsen et al. | 47/57.6 |
| 4,802,305 | 2/1989 | Kojimoto et al. | 47/57.6 |
| 4,806,357 | 2/1989 | Garrett et al. | 427/4 |
| 4,808,430 | 2/1989 | Kouno | 427/4 |
| 4,866,096 | 9/1989 | Schweighardt | 514/756 |
| 4,879,839 | 11/1989 | Gago et al. | 47/57.6 |
| 5,010,685 | 4/1991 | Sakamoto et al. | 47/57.6 |
| 5,044,116 | 9/1991 | Gago et al. | 47/57.6 |
| 5,236,469 | 8/1993 | Carlson et al. | 47/57.6 |
| 5,284,765 | 2/1994 | Bryan et al. | 435/240.4 |

FOREIGN PATENT DOCUMENTS

| | | |
|---|---|---|
| 1241552 | 9/1988 | Canada. |
| 1250296 | 2/1989 | Canada. |
| 0 107 141 | 5/1984 | European Pat. Off.. |
| 0 380 692 | 8/1990 | European Pat. Off.. |
| 61-040708 | 2/1986 | Japan. |
| 62-275604 | 11/1987 | Japan. |
| 63-133904 | 6/1988 | Japan. |
| 63-152905 | 6/1988 | Japan. |
| 2046240 | 2/1990 | Japan. |
| WO 91/01803 | 2/1991 | WIPO. |

OTHER PUBLICATIONS

Redenbaugh et al., "Encapsulation of Somatic Embryos in Synthetic Seed Coats," *HortScience* 21 (No. 3, Section 2): 819–820 (1986) (Abstract of presentation at XXII Int'l Hortic. Cong., Aug. 10–18, 1986, Davis, CA).

Redenbaugh et al., "Encapsulation of Somatic Embryos for Artificial Seed Production" (Abstract), *In Vitro* 20 (Part 2): 256–257 (1984).

Fujii et al., "Improving Plantlet Growth and Vigor from Alfalfa Artificial Seed" (Abstract), *In Vitro* 24 (No. 3, Part 2):70A (1989).

Fujii et al., "ABA Maturation and Starch Accumulation in Alfalfa Somatic Embryos" (Abstract), *In Vitro* 25 (No. 3, Part 2):61A (1989).

Janick, "Production of Synthetic Seed via Desiccation and Encapuslation" (Abstract), *In Vitro* 24 (No. 3, Part 2):70A (1989).

Kamada et al., "New Methods for Somatic Embryo Induction and Their Use for Synthetic Seed Production" (Abstract), *In Vitro* 24 (No. 3, Part 2): 71A (1988).

Bapat and Rao, "Sandalwood Plantlets from 'Synthetic Seeds,'" *Plant Cell Reports* 7:434–436 (1988).

Datta and Potrykus, "Artificial Seeds in Barley: Encapsulation of Microspore–Derived Embryos," *Theor. Appl. Genet.* 77:820–824 (1989).

(List continued on next page.)

*Primary Examiner*—David T. Fox
*Assistant Examiner*—Melissa L. Kimball
*Attorney, Agent, or Firm*—Klarquist Sparkman Campbell Leigh & Whinston, LLP

[57] ABSTRACT

A manufactured seed is disclosed which comprises a plant embryo preferably encapsulated, or at least in contact with, a hydrated oxygenated gel. The gel can be oxygenated by passing oxygen gas through a gel solution before curing the gel or by exposing the gel to oxygen gas after curing. The gel is preferably oxygenated by adding to an uncured gel solution a suitably stabilized emulsion of a perfluorocarbon compound or a silicone oil, which compounds are capable of absorbing large amounts of oxygen, and are non-toxic and inert. The seed analog can further comprise an outer shell at least partially surrounding the gel and embryo, thereby forming a capsule. The outer shell preferably is shaped to aid the radical of a germinating embryo in protrusively rupturing the capsule, thereby facilitating successful germination and minimizing incidence of seedling malformation. Other shell materials are selected to provide requisite rigidity to the capsule while imparting minimal restriction to successful germination. In a preferred embodiment for germinating embryos having cotyledon(s), at least the cotyledons are enclosed in a porous material resistant to penetration by the growing cotyledon(s), and the embryo and porous enclosure are encapsulated in a hydrated gel.

32 Claims, 15 Drawing Sheets

OTHER PUBLICATIONS

Fujii et al., "Artificial Seeds for Plant Propagation," *Trends in Bio/Technol.* 5:335–339 (1987).

Gupta and Durzan, "Biotechnology of Somatic Polyembryogenesis and Plantlet Regeneration in Loblolly Pine," *Bio/Technol.* 5:147–151 (1987).

Ibarbia, "Synthetic Seed: Is it the Future," *Western Grower and Shipper* 59:12 (1988).

Kim and Janick, "ABA and Polyox–Encapsulation or High Humidity Increases Survival of Desiccated Somatic Embryos of Celery," *HortScience* 24:674–676 (1989).

Kitto and Janick, "Production of Synthetic Seeds by Encapsulating Asexual Embryos of Carrot," *J. Amer. Soc. Hort. Sci.* 110:277–282 (1985).

Kitto and Janick, "A Citrus Embryo Assay to Screen Water–Soluble Resins as Synthetic Seed Coats," *HortScience* 20:98–100 (1985).

Redenbaugh et al. "Encapsulated Plant Embryos," *Advances in Biotechnical Processes* 9:225–248 (1988).

Redenbaugh et al., "Somatic Seeds: Encapsulation of Asexual Plant Embryos," *Bio/Technol.* 4:797–801 (1986).

Redenbaugh et al., "Encapsulation of Somatic Embryos in Synthetic Seed Coats," *HortScience* 22:803–809 (1987).

Redenbaugh et al., "Scale–Up: Artificial Seeds," in Green et al. (eds.), *Plant Tissue and Cell Culture*, pp. 473–493, Alan R. Liss, NY (1987).

Rogers, "Synthetic–Seed Technology," *Newsweek*, Nov. 28, 1983.

Stuart and Redenbaugh, "Use of Somatic Embryogenesis for the Regeneration of Plants," in LaBaron et al. (eds.), *Biotechnology in Agricultural Chemistry*, Ch. 6, pp. 87–96, American Chemical Society, Washington, DC (1987).

Teasdale and Buxton, "Culture of *Pinus radiata* Embryos with Reference to Artificial Seed Production," *New Zealand J. For. Sci.* 16:387–391 (1986).

Clark et al., "Emulsions of Perfluorinated Solvents for Intravascular Gas Transport," *Fed. Proceed.* 34:1468–1477 (1975).

Riess and Le Blanc, "Perfluoro Compounds as Blood Substitutes," *Angew. Chem. Int. Ed. Engl.* 17:621–634 (1978).

Davis et al., "Novel Compositions of Emulsified Perfluorocarbons for Biological Applications," *Brit. J. Pharmacol.* 89:665P (1986).

"Fluorinert™ Electronic Liquids" brochure, 3M Industrial Chemical Products Division, St. Paul, Minnesota (1989).

"Flourinert™ Electronic Liquids for Direct Contact Dielectric Cooling" brochure, 3M Industrial Chemical Products Division, St. Paul, Minnesota (1986).

Chandler et al., "Effects of Emulsified Perfluorochemicals on Growth and Ultrastructure of Microbial Cells in Culture," *Biotechnol. Letters* 9:195–200 (1987).

King et al., "Perfluorochemicals and Cell Culture," *Biotechnol.* 7:1037–1042 (1989).

Clark et al., "The Physiology of Synthetic Blood," *J. Thorac & Cardiovasc. Surg.* 60:757–773 (1970).

Fujita et al., "Fluorocarbon Emulsion as a Candidate for Artificial Blood," *Europ. Surg. Res.* 3:436–453 (1971).

Geyer, R.P., "'Bloodless' Rats Through the Use of Artificial Blood Substitutes," *Fed. Proceed.* 34:1499–1505 (1975).

Senaratna, "Artificial Seeds," *Biotech. Adv.* 10:379–392 (1992).

Adlercreutz and Mattiasson, "Oxygen Supply to Immobilized Cells: 1. Oxygen Production by Immobilized *Chlorella pyrenoidosa*," *Enzyme Microbiol. Technol.* 4:332–336 (1982).

Aldercreutz and Mattiasson, "Oxygen Supply to Immobilized Biocatalysts. A Model Study," *Acta Chem. Scand.* B36:651–653 (1982).

Adlercreutz and Mattiasson, "Oxygen Supply to Immobilized Cells. 3. Oxygen Supply by Hemoglobin or Emulsions of Perfluorochemicals," *Eur. J. Appl. Microbiol. & Biotechnol.* 16:165–170 (1982).

Mattiasson and Aldercreutz, "Use of Perfluorochemicals for Oxygen Supply to Immobilized Cells," *Ann. N.Y. Acad. Sci.* 413:545–547 (1984).

Damiano and Wang, "Novel Use of a Perfluorocarbon for Supplying Oxygen to Aerobic Submerged Cultures," *Biotechnol. Letters* 7:81–86 (1985).

Redenbaugh et al., "III.3 Artificial Seeds—Encapsulated Somatic Embryos," *Biotech. in Agr. & For.* 17:395–416 (1991).

Bapat et al., "In Vivo Growth of Encapsulated Axillary Buds of Mulberry, (*Morus indica* L.)," *Plant Cell, Tissue and Organ Culture* 20:69–70 (1990).

Li, "Somatic Embryogenesis and Synthetic Seed Technology Using Carrot as a Model System," in *Synseeds: Applications of Synthetic Seeds to Crop Improvement*, Redenbaugh, Ed., CRC Press, Florida (1993), chap. 16.

Sanada et al., "Celery and Lettuce," in *Synseeds: Applications of Synthetic Seeds to Corp Improvement*, Redenbaugh, Ed., CRC Press, Florida (1993), chap. 17.

Bapat, "Studies on Synthetic Seeds of Sandalwood (*Santalum album* L.) and Mulberry (*Morus indica* L.)," in *Synseeds: Applications of Synthetic Seeds to Crop Improvement*, Redenbaugh, Ed., CRC Press, Florida (1993), chap. 21.

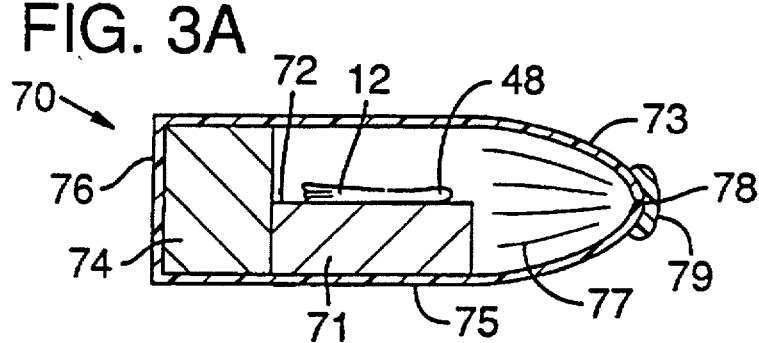
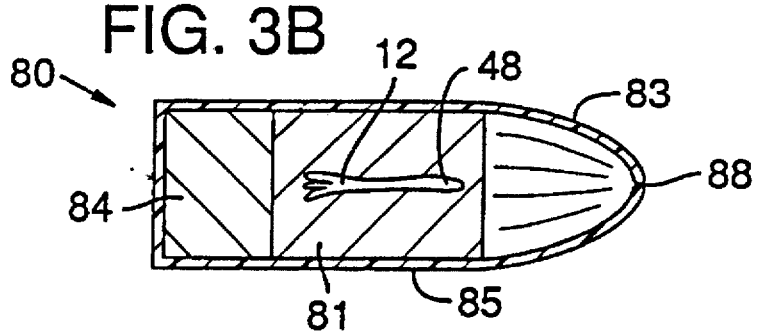
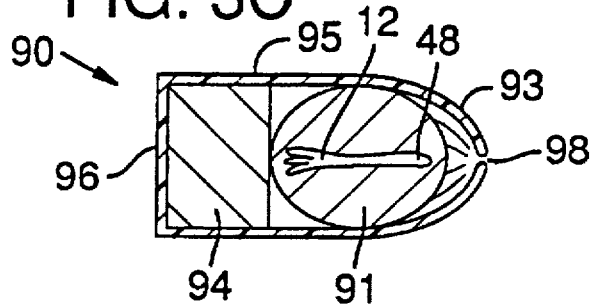
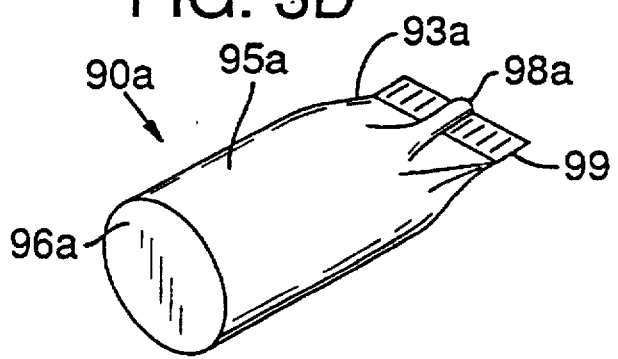

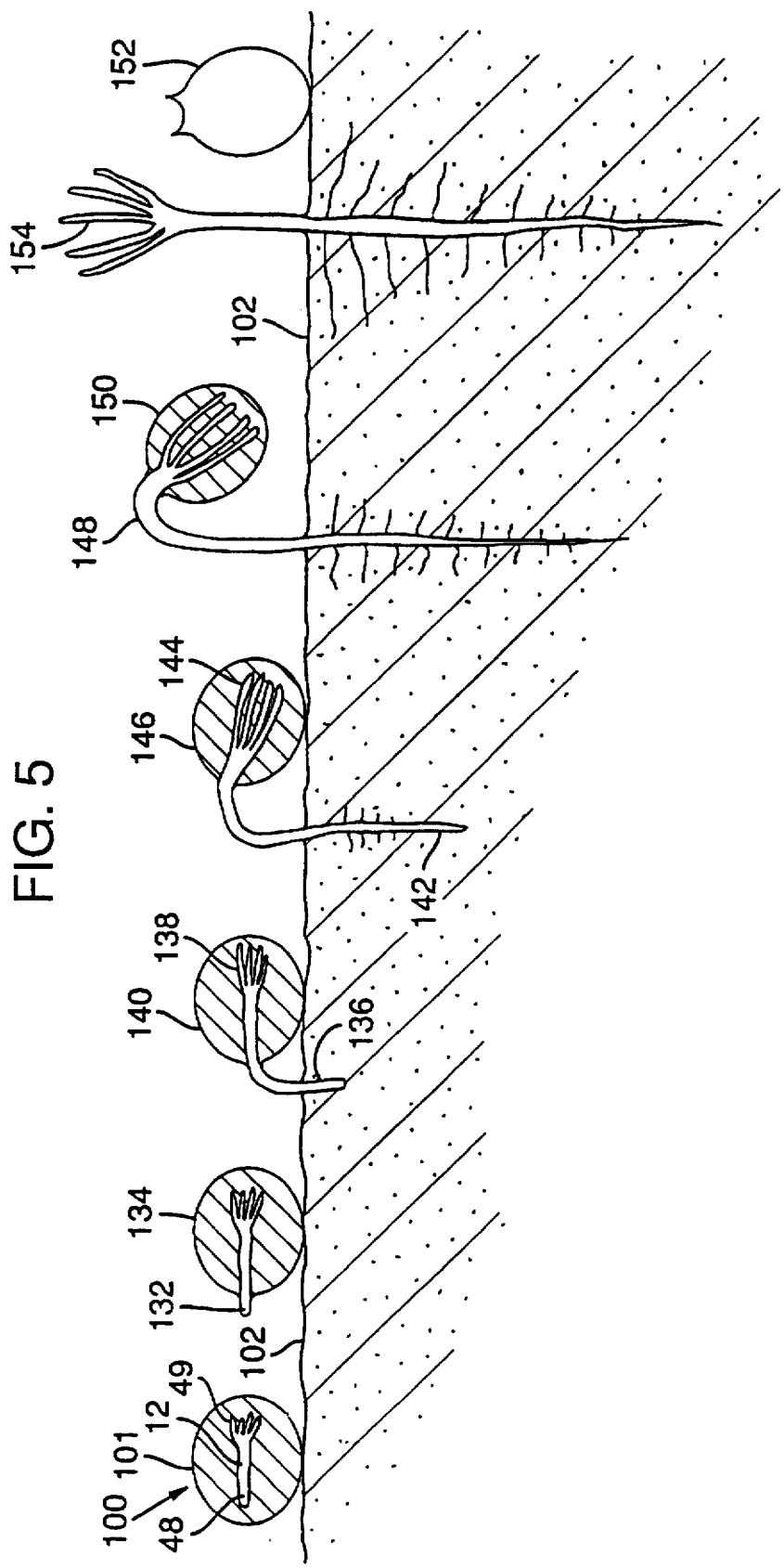

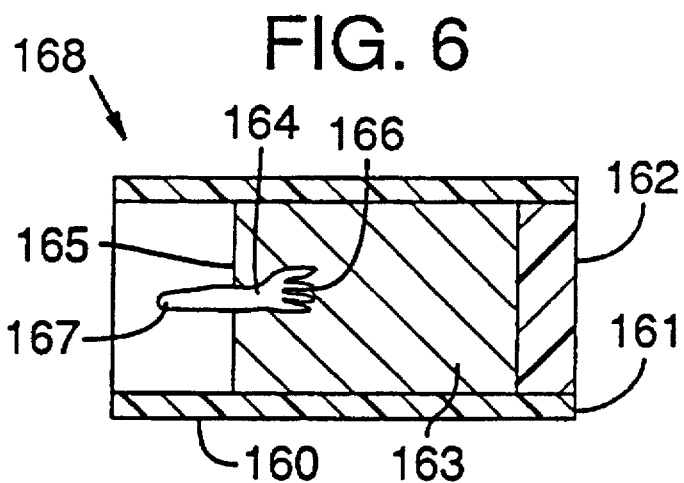
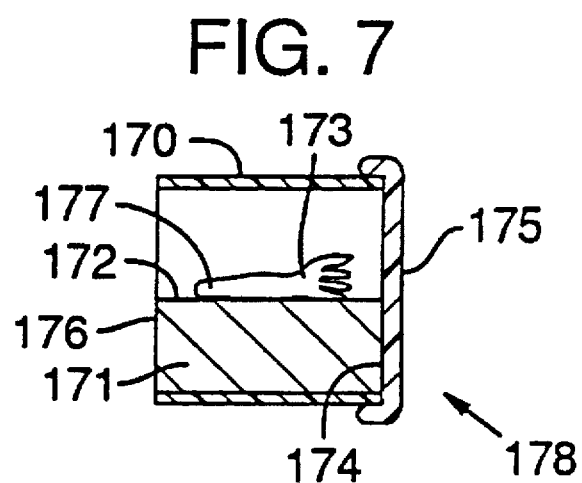
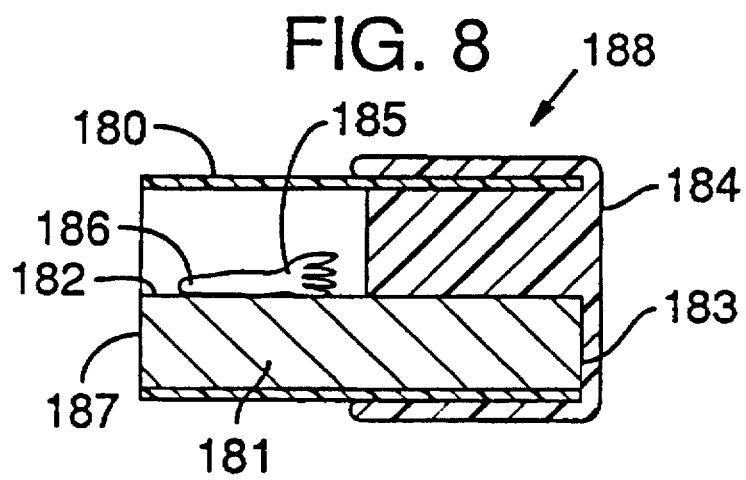

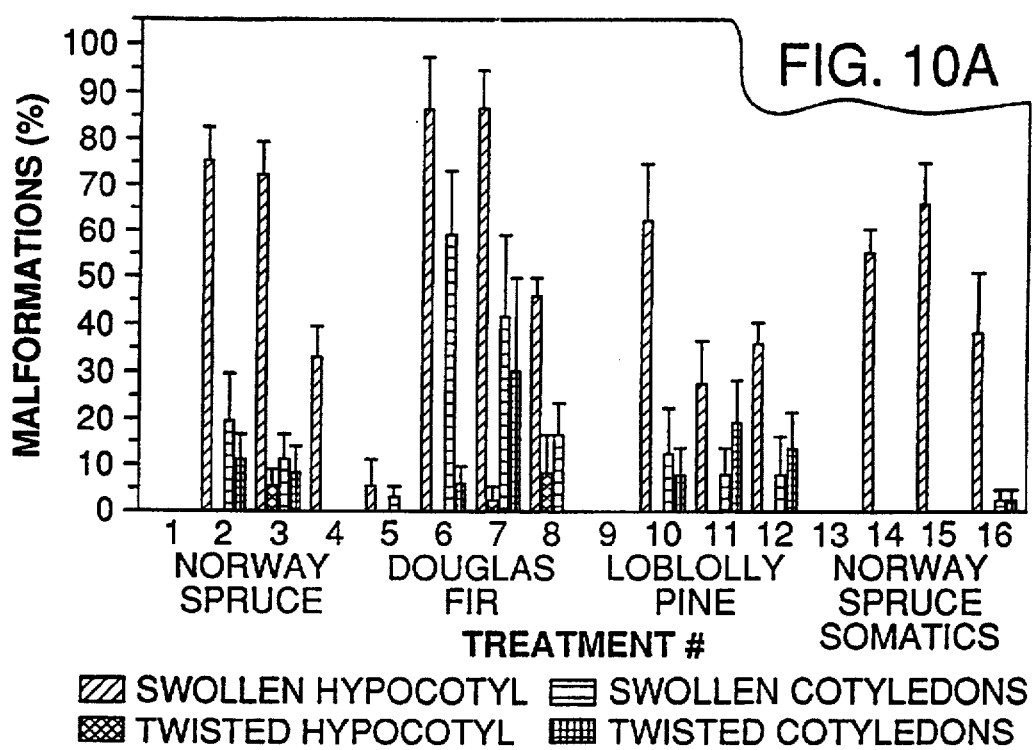
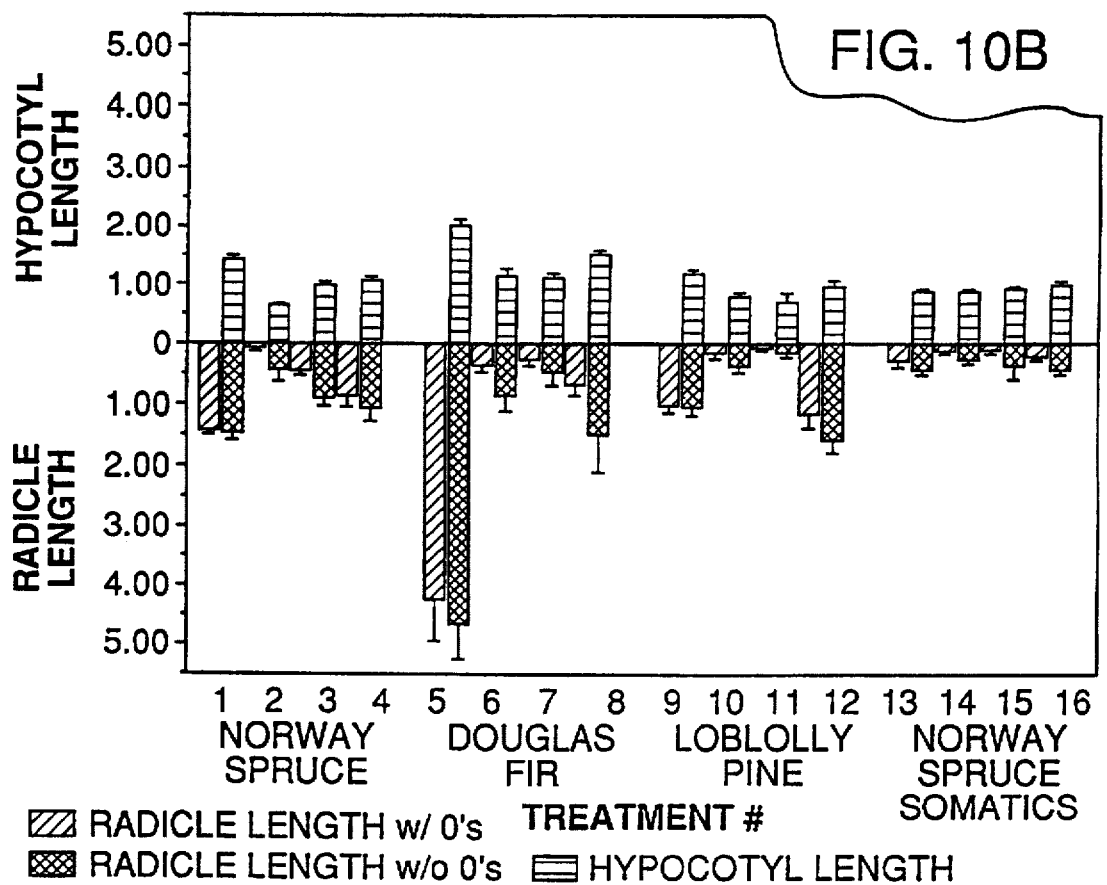

MANUFACTURED SEED COTYLEDON RESTRAINT

This a continuation of application Ser. No. 07/781,773, filed Oct. 23, 1991, now U.S. Pat. No. 5,427,593, which was a continuation-in-part application of prior application Ser. No. 07/604,656, filed Oct. 26, 1990, now U.S. Pat. No. 5,236,469.

FIELD OF THE INVENTION

This invention relates to a method for propagating plants. More particularly, it relates to methods for producing plant reproductive units, each containing a propagated plant embryo, capable of being sown like natural seeds.

BACKGROUND OF THE INVENTION

Modern agriculture, including silviculture, often requires the planting of large numbers of substantially identical plants genetically tailored to grow optimally in a particular locale or to possess certain other desirable traits. Production of new plants by sexual reproduction, which yields botanic seeds, can be slow and is often subject to genetic recombinational events resulting in variable traits in the progeny. Also, such crossing is time- and labor-intensive. Further, inbred strains such as those used to perform such crosses often lack vigor, resulting in low seed productivity.

Despite the drawbacks of conventional crossbreeding by sexual means, botanic seeds produced by such methods have an important advantage in that each seed comprises food-storage organs and protective structures that shelter the plant embryo inside the seed from the harsh soil environment and nurture the embryo during the critical stages of sowing and germination. Without such organs and structures, the plant embryo would be incapable of surviving in nature until it grew to seedling size.

In view of the disadvantages of producing large numbers of identical progeny plants by sexual means, propagation of commercially valuable plants via culturing of somatic or zygotic plant embryos has been intensively studied. Such "asexual" propagation has been shown for some species to yield large numbers of genetically identical embryos each having the capacity to develop into a normal plant. Unfortunately, these embryos, which are produced under laboratory conditions, lack the protective and nutritive structures found in seeds. As a result, the embryos must usually be further cultured under laboratory conditions until they reach an autotrophic "seedling" state characterized by an ability to produce their own food via photosynthesis, resist desiccation, produce roots able to penetrate soil, and fend off soil microorganisms. Such extensive laboratory culture during several distinct stages in plant development is time-consuming, resource-intensive, and requires skilled labor.

Some researchers have experimented with the production of "artificial" seeds in which individual plant somatic or zygotic embryos are encapsulated in a hydrated gel. (As used herein, "hydrated" denotes the presence of free water interspersed throughout the matrix of gel molecules comprising the gel capsule.) This method evolved from other work showing that encapsulating seeds in hydrated gels can improve germination in some species, especially since such gels can be supplemented with plant hormones and other compounds that aid germination and improve seedling survival in the field. With respect to artificial seeds, reference is made to European Patent application No. 0,107,141 to Plant Genetics, Inc., published on May 2, 1984 (claiming priority under U.S. Pat. No. 4,562,663, filed on Oct. 12, 1982), teaching that hydrated gels used to encapsulate plant embryos should permit gas diffusion from the environment to the embryo and protect the embryo from abrasion. A suitable gel can be selected from alginates, guar gums, agar, agarose, gelatin, starch, polyacrylamide, and other gels. The gel can include additives such as plant nutrients, pesticides, and hormones. If necessary, the gel can be surface-hardened to confer further resistance to abrasion and penetration.

While a hydrated gel capsule seems to provide adequate moisture for a plant embryo and satisfactory protection against physical trauma in some instances, it has a poor permeability to atmospheric gases, especially oxygen, necessary for survival and growth of the embryo. As a result, there has been some effort directed to increasing the amount of oxygen inside the capsule. U.S. Pat. No. 4,808,430 to Kuono discloses encapsulating a seed in a hydrated gel along with an air bubble. Unfortunately, such a bubble actually contains a very small volume of air which in many instances does not provide enough oxygen for proper germination. This is especially the case when such bubble-containing capsules are stored for a length of time at room temperature. At room temperature, embryos of many types of plants respire, even if not actually germinating, which consumes oxygen. Since a hydrated gel is a poor absorber of atmosphere oxygen, the embryo in the seed soon becomes oxygen-starved despite a presumably initially adequate supply in the bubble. As a result, no oxygen is left after such storage to support germination.

The drawbacks of including an air bubble along with an encapsulated seed would not be fully rectified by encapsulating an embryo or seed in a foamed gel containing multiple air bubbles. The actual area available for gas exchange between the surrounding atmosphere, the gel capsule, the air bubbles, and the embryo is still quite small in a foamed gel. Such a small area, in combination with the low transfer rate of oxygen between air and a hydrated gel, would yield too low a rate of oxygen delivery to the embryo, especially during germination when oxygen requirements rapidly escalate.

Another problem with artificial seeds to date is the low numbers of successful germinants, particularly "normal" germinants, producible therefrom. Although many factors probably can cause abnormal germination, these results generally indicate that artificial seeds as currently known in the art do not accurately simulate important physical parameters present in natural seeds such as the manner and degree to which the embryo is restrained within the artificial seed.

Hence, there is a need for an analog of botanic seed comprising a plant embryo in contact with a hydrated gel having an elevated concentration of oxygen.

There is also a need for an analog of botanic seed which better simulates the natural way in which the plant embryo is restrained within a seed.

There is also a need for an analog of botanic seed which exhibits an increased number of successful normal germinants therefrom.

SUMMARY OF THE INVENTION

In accordance with one aspect of the present invention, an analog of botanic seed is provided which comprises a plant embryo or other unit of totipotent plant tissue encapsulated, or at least in contact with, a hydrated oxygenated gel. The gel preferably also includes dissolved nutrients and other beneficial compounds such as vitamins, hormones, and sources of carbon and energy, which can be utilized by the germinating embryo for enhanced growth or improved probability of survival. Suitable gel solutes are substantially non-phytotoxic and can be selected from a number of different types such as, but not limited to, sodium alginate, agar, agarose, amylose, pectins, dextran, gelatin, starch, modified celluloses, and polyacrylamide. Thus, the gel serves as an "artificial gametophyte" for the embryo in a manner analogous to the gametophyte portion of a natural botanic seed.

It is to be understood that the term "artificial gametophyte" denotes that the gel serves as an artificial endosperm or other seed nutritive tissue, depending upon the origin of the totipotent plant tissue.

Embryos of different species of plants require different amounts of oxygen to undergo germination. Hence, an "oxygenated" gel as used herein has a concentration of oxygen that is higher than the concentration of oxygen, at standard temperature and pressure, that would otherwise be absorbed from the atmosphere. An "oxygen-carrying" gel is a similar type of gel containing any extraneously added oxygen-absorbing or oxygen-carrying substance. Therefore, an oxygen-carrying gel is a type of oxygenated gel.

One way of achieving oxygenation of a gel according to the present invention is to bubble oxygen gas through a gel solution before curing the gel. Alternatively, gel capsules can be oxygenated by exposure to oxygen, under pressure if necessary, after curing.

Oxygenation of the gel is preferably enhanced by adding to an uncured gel solution a suitably stabilized emulsion of an oxygen-carrying or oxygen-absorbing compound, selected from the group consisting of perfluorocarbons and silicone oils. Representative perfluorocarbons include perfluorocycloalkanes, perfluoro(alkylcycloalkanes), perfluoro(alkylsaturated heterocyclics), and perfluoro(tert-amines). These types of compounds are capable of absorbing large amounts of oxygen, and are also inert and substantially non-toxic.

The emulsion is preferably stabilized by adding a substantially non-phytotoxic surfactant to a mixture of the gel solution and perfluorocarbon or silicone. Representative surfactants include methyl oxirane polymers, egg albumin, and other substantially non-phytotoxic surfactants such as those for food or ingestible pharmaceutical use.

The concentration of perfluorocarbon (or silicone oil) can depend on the oxygen requirements of the plant species being encapsulated in the gel, the oxygen-carrying capability of the perfluorocarbon (or silicone oil) being used, the type of gel, or the size of the microdroplets comprising the emulsion. Generally, the concentration of the perfluorocarbon (or silicone oil) in the gel is about 15% w/v or less and the concentration of silicone oil in the gel is about 30% w/v or less.

The concentration of surfactant is dependent upon the surfactant being used and the size of the microdroplets comprising the emulsion. As the diameter of the droplets in a unit volume of perfluorocarbon emulsion is decreased, the surface area of the disperse phase is increased, and correspondingly more surfactant is required to suitably stabilize the emulsion. Generally, the concentration of surfactant is about 10% w/v or less.

A seed analog according to the present invention preferably includes some provision for "cotyledon restraint." That is, as the embryo begins to grow in the seed analog in preparation for germination therefrom, the cotyledon(s) of the embryo are prevented from growing into and becoming entrapped in the gel. Preferred cotyledon restraint means include, but are not limited to, any of various porous, tubelike structures surrounding and contacting the embryo; particularly the cotyledon(s) of the embryo. The porous tube, in turn, is situated in a cavity in the gel. The porous tube allows transfer of water, nutrients, and oxygen from the gel to the embryo. The cotyledons are oriented in the porous tube toward a closed end and the radical is oriented toward an open end that can be weakly covered to avoid desiccation. As the cotyledon(s) elongate during germination, they impinge upon the closed end of the tube, preventing cotyledon entrapment and urging the radical to emerge from the open end of the porous tube. Thus, the germinating embryo emerges from the seed analog in a manner similar to germination of a natural botanic seed.

An analog of botanic seed according to the present invention can also include a rigid outer shell for increased protection against desiccation and physical trauma. The outer shell can have a tapered or wedge-shaped end to facilitate emergence of the radical during germination. The outer shell can also have an orifice or analogous feature, or readily breaks apart during germination, making it relatively easy for the embryonic radical to burst from the analog during germination. The outer shell can be fabricated from a variety of materials including, but not limited to, cellulosic materials, glass, plastic, cured polymeric resins, paraffin, and combinations thereof.

The outer shell can further comprise plural layers, where the inner layer thereof can comprise a relatively compliant and water-impermeable cellulosic material and the outer layer can comprise a polymeric material having a high dry strength and a low wet strength. Alternatively, the inner layer can comprise a rigid shape such as an open-ended cylinder, where at least a portion of said open ends is covered with an outer-layer material having a high dry strength and a low wet strength.

Further alternatively, the outer shell can comprise a relatively compliant cellulosic or analogous material, shaped to at least-partially conform to the shape of the hydrated oxygenated gel capsule therein, and having at least one tapered end. The tapered end terminates with an orifice which is preferably covered with a polymeric material having a high dry strength and low wet strength.

Although the embryo-containing gel unit preferably contains nutrients dissolved therein, it is possible to dissolve the nutrients in a separate nutrient-containing unit in contact with the embryo-containing gel unit. The nutrient-containing unit can be comprised of any substantially non-phytotoxic substance that will allow nutrients therein to be transferred via water to the embryo-containing unit. Representative substances include, but are not limited to, water, a gel similar to that in the embryo-containing unit, vermiculite, perlite, or any polymeric material that is non-toxic and will release the nutrients readily over a period of time. For example, the nutrients may be microencapsulated in a manner known in the art.

It is therefore an object of the present invention to provide analogs of botanic seed characterized by a high percent germination of plant embryos therefrom.

A further object is to provide such an analog comprising a unit of totipotent plant tissue encapsulated, or at least in contact with, a hydrated oxygenated gel to provide sufficient oxygen to enable the unit of totipotent plant tissue to successfully germinate.

A further object is to provide such an analog containing an increased concentration of oxygen over the concentration of oxygen that would normally be present in hydrated gels by absorption of oxygen from the atmosphere.

A further object is to provide such an analog with an outer shell for increased protection of the gel and embryo from desiccation and physical trauma but which facilitates the maintenance of elevated oxygen levels within the seed analog while allowing the germinant to burst out of seed analog during germination.

A further object is to provide such an analog with proper cotyledon restraint to enable the embryo to germinate from the analog in a manner resembling normal germination from a seed.

The foregoing objects and other features and advantages of the present invention will be more fully understood as the detailed description thereof proceeds, particularly when considered together with the accompanying drawing.

BRIEF DESCRIPTION OF THE DRAWING

FIG. 3A is a cross-sectional view of an analog of botanic seed usable in a mechanical sowing process.

FIG. 3B is a cross-sectional view of an alternative embodiment of the analog of botanic seed shown in FIG. 3A.

FIG. 3C is a cross-sectional view of another alternative embodiment to the analog of botanic seed shown in FIG. 3A.

FIG. 3D is an isometric view of the exterior of an alternative embodiment to that shown in FIG. 3C.

FIG. 5 is a stepwise sequential diagram similar to FIG. 4 but wherein the gel capsule remains attached for a time to the germinating embryo.

FIG. 6 is a cross-sectional diagram of the analog of the botanic seed evaluated as Treatment (2) of Example 4.

FIG. 7 is a cross-sectional view of an analog of botanic seed evaluated as Treatment (4) of Example 4.

FIG. 8 is a cross-sectional view of an analog of botanic seed evaluated as Treatment (6) of Example 4.

FIG. 10A is a bar graph showing percent malformations of various embryonic structures of several species of gymnosperms after germination from capsules, as evaluated in Example 7.

FIG. 10B is a bar graph showing radical and hypocotyl lengths of the germinating embryos evaluated in Example 7.

DETAILED DESCRIPTION OF THE INVENTION

Totipotent Plant Tissue

Figure 1A:
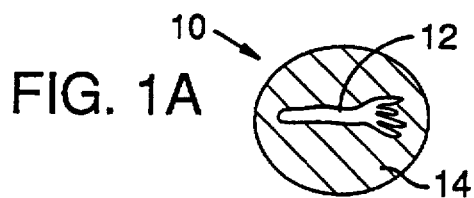
FIG. 1A is a cross-sectional view of one embodiment of an analog of botanic seed according to the present invention comprising an embryo encapsulated in a hydrated oxygenated gel.

An analog of botanic seed, according to one aspect of the present invention, comprises a unit of totipotent plant tissue having at least one surface in contact with a cured, hydrated, oxygenated gel.

As used herein, "totipotent" refers to a capacity to grow and develop into a normal plant. Totipotent plant tissue has both the complete genetic information of a plant and the ready capacity to develop into a complete plant if cultured under favorable conditions. Totipotent plant tissue is obtainable from several areas of a plant, such as meristematic tissue and plant embryonic tissue.

Meristematic tissue is comprised of undifferentiated plant cells that divide to yield other meristematic cells as well as differentiated cells that elongate and further specialize to form structural tissues and organs of the plant. Meristematic tissue is located, for example, at the extreme tips of growing shoots or roots, in buds, and in the cambium layer of woody plants.

Plant embryonic tissue can be found (in the form of a "zygotic" embryo) inside a botanic seed produced by sexual reproduction. Also, plant "somatic" embryos can be produced by culturing totipotent plant cells such as meristematic tissue under laboratory conditions in which the cells comprising the tissue are separated from one another and urged to develop into minute complete embryos. Alternatively, a process termed "cleavage polyembryony" known in the art can be induced during natural embryo development in seed. For simplicity, totipotent plant tissue is referred to herein simply as the "embryo", unless stated otherwise.

As used herein, a "unit" of plant meristematic tissue or plant embryonic tissue is a piece of such tissue that can be individually handled, placed on or encapsulated in a gel according to the present invention, and which will develop into a germinant and ultimately a plant under favorable conditions.

Gels

The material used to encapsulate the totipotent plant tissue is a hydrated gel. A "gel" is a substance that is prepared as a colloidal solution and that will, or can be caused to, form a semisolid material. Such conversion of a liquid gel solution into a semisolid material is termed herein "curing" or "setting" of the gel. According to the present invention, the hydrated gel, along with any other substances included therein, serves as an "artificial gametophyte" for the totipotent plant tissue.

As used herein, "hydrated" denotes water-containing. Such gels are prepared by first dissolving in water (where water serves as the solvent, or "continuous phase") a hydrophilic polymeric substance (serving as the solute, or "disperse phase") that, upon curing, combines with the continuous phase to form the semisolid material. In other words, the water becomes homogeneously associated with the solute molecules without experiencing any substantial separation of the continuous phase from the disperse phase. However, water molecules can be freely withdrawn from a cured hydrated gel, such as by evaporation or imbibition by a germinating embryo. When cured, these gels have the familiar characteristic of compliant solids, like a mass of gelatin, where the compliance becomes progressively less and the gel becomes more "solid" to the touch as the relative amount of water in the gel is decreased.

In addition to being water-soluble, suitable gel solutes are neither cytotoxic nor substantially phytotoxic. As used herein, a "substantially non-phytotoxic" substance is a substance that does not interfere substantially with normal plant development, such as by killing a substantial number of plant cells, substantially altering cellular differentiation or maturation, causing mutations, disrupting a substantial number of cell membranes or substantially disrupting cellular metabolism, or substantially disrupting other process.

Candidate gel solutes include, but are not limited to, the following: sodium alginate, agar, agarose, amylose, pectin, dextran, gelatin, starch, amylopectin, modified celluloses such as methylcellulose and hydroxyethylcellulose, and polyacrylamide. Other hydrophilic gel solutes can also be used, so long as they possess similar hydration and gelation properties and lack of toxicity. Also, it is important to be able to add other substances such as plant nutrients or emulsified materials to a gel without substantially interfering with gelling ability. Further, a cured gel must have sufficient strength to maintain the integrity of the capsule without the capsule being so durable that a germinating embryo cannot penetrate it.

Gels are typically prepared by dissolving a gel solute, usually in fine particulate form, in water to form a gel solution. Depending upon the particular gel solute, heating is usually necessary, sometimes to boiling, before the gel solute will dissolve. Subsequent cooling will cause many gel solutions to reversibly "set" or "cure" (become gelled). Examples include gelatin, agar, and agarose. Such gel solutes are termed "reversible" because reheating cured gel will re-form the gel solution. Solutions of other gel solutes require a "complexing" agent which serves to chemically cure the gel by crosslinking gel solute molecules. For example, sodium alginate is cured by adding calcium nitrate ($Ca(NO_3)_2$) or salts of other divalent ions such as, but not limited to, calcium, barium, lead, copper, strontium, cadmium, zinc, nickel, cobalt, magnesium, and iron to the gel solution. Many of the gel solutes requiring complexing agents become irreversibly cured, where reheating will not re-establish the gel solution.

The concentration of gel solute required to prepare a satisfactory gel for encapsulation purposes according to the present invention varies depending upon the particular gel solute. For example, a useful concentration of sodium alginate is within a range of about 0.5% w/v to about 2.5% w/v, preferably about 0.9% w/v to 1.5% w/v. A useful concentration of agar is within a range of about 0.8% w/v to about 2.5% w/v, preferably about 1.8% w/v. (As used herein, the "% w/v" concentration unit is equivalent to grams of solute per 100 mL of solvent.) Gel concentrations up to about 24% w/v have been successfully employed for other gels. In general, gels cured by complexing require less gel solute to form a satisfactory gel than "reversible" gels.

It is preferable to provide the embryo with the usual spectrum of plant nutrients and other beneficial substances such as vitamins and a source of carbon and energy (herein collectively termed generally "nutrients") while the embryo is encapsulated in the gel. Typical ways of providing nutrients are to dissolve the gel solute in a solution of the nutrients or to add a volume of concentrated nutrient solution to the gel solution before curing the gel. In this way, when the gel sets ("cures"), any areas of the embryo in contact with the gel are also in direct contact with nutrient solutes, where the nutrient solutes are present in substantially uniform concentrations throughout the gel. Another way to provide nutrients is to place a gel capsule containing the embryo but lacking nutrients in contact with a second mass of the same or a different type of hydrated gel which does contain nutrients. As a result of a nutrient concentration gradient between the two hydrated gel masses, nutrients will migrate from the nutrient-containing gel mass to the embryo-containing gel mass.

Another possible way to provide nutrients is to place a gel unit containing the embryo but lacking nutrients in contact with a second unit comprising microencapsulated nutrients or nutrients associated with any substantially non-phytotoxic substance that will allow nutrients dissolved therein to be transferred via water to the embryo-containing gel unit. Representative materials include, but are not limited to, water, a gel similar to the gel in the embryo-containing unit, vermiculite, perlite, or any polymeric material that is non-toxic and will release the nutrients readily over a period of time.

A number of possible nutrient formulations exist in the art, including a number of proprietary formulations. For example, a popular medium is the "MS liquid" (Murashige and Skoog, *physiologia Plantarum* 15:473–497 (1962)) containing the following dissolved in water:

| | |
|---|---|
| NH$_4$NO$_3$ | 1650 mg/L |
| KNO$_3$ | 1900 mg/L |
| CaCl$_2$ 2H$_2$O | 440 mg/L |
| MgSO$_4$ 7H$_2$O | 370 mg/L |
| KH$_2$PO$_4$ | 170 mg/L |
| Na$_2$EDTA | 37.25 mg/L |
| FeSO$_4$ 7H$_2$O | 27.85 mg/L |
| MnSO$_4$ 4H$_2$O | 22.3 mg/L |
| ZnSO$_4$ 4H$_2$O | 8.6 mg/L |
| H$_3$BO$_3$ | 6.2 mg/L |
| KI | 0.83 mg/L |
| Na$_2$MoO$_4$ 2H$_2$O | 0.25 mg/L |
| CuSO$_4$ 5H$_2$O | 0.025 mg/L |
| CoCl$_2$ 6H$_2$O | 0.025 mg/L |
| Glycine | 0.2 mg/100 cm$^3$ |
| Nicotinic Acid | 0.05 mg/100 cm$^3$ |
| Pyridoxine HCl | 0.05 mg/100 cm$^3$ |
| Thiamine HCl | 0.01 mg/100 cm$^3$ |
| Kinetin | 0.1 mg/L |
| Myo-inositol | 100 mg/L |
| IAA | 10 mg/L |
| Sucrose | 30000 mg/L |
| pH | 5.7–5.8 |

(Note: An "MS medium" will also contain 1.0% w/v agar. Murashige and Skoog, id.) Of course, when adding a nutrient solution to a gel solution, the concentrations of both solutions should be high enough such that the resulting mixture of the two solutions has the proper concentrations of gel and nutrients.

The nutrient solution can also include plant growth hormones and other compounds serving to further increase the probability of germinant survival.

As used herein, a "nutrient liquid" is an aqueous solution of nutrients similar to the "MS liquid" formulation. A "nutrient agar" is similar to the "MS medium." Changes in types and amounts of certain ingredients can be made to meet the needs of specific types of plants without departing in any substantial manner from the purpose and utility of a nutrient liquid or nutrient medium.

Since nutrient media, nutrient liquids, and any nutrient-containing gel is a rich growth medium for microorganisms and fungi, it is important that all such liquids, as well as the embryos themselves, be sterile before use. Embryos are kept sterile by culturing under sterile conditions. Liquids can be autoclaved or microfiltered.

Oxygenated Gels

As used herein, an "oxygenated" gel has a concentration of oxygen therein that is higher than the concentration of oxygen at standard temperature and pressure that would be present in the gel as a result only of absorption from the atmosphere. An "oxygen-carrying" gel as used herein is one that has any extraneously-added oxygen-absorbing or oxygen-carrying substances. Thus, an oxygen-carrying gel is a type of oxygenated gel.

Oxygenation of a gel can be achieved by several methods. First, a gel solution can be oxygenated before curing by passing oxygen gas through the solution. In a laboratory, this can be performed by placing the solution in a "gas-washing bottle" known in the art and bubbling oxygen gas through the solution while the solution is in the bottle. Analogous methods can be employed for oxygenation of large volumes and for oxygenation of a continuous stream of uncured gel. When oxygenating a gel solution in this manner, it should be kept in mind that hot solutions generally absorb less oxygen than cold solutions. Second, as described in further detail hereinbelow, a gel can be oxygenated after curing by, for example, placing the gel in a pressurized oxygen, oxygen-enriched or pure oxygen environment. These methods are also effective when the gel contains oxygen-carrier or oxygen-absorbing compounds.

The concentration of oxygen in an oxygenated gel will depend on a number of factors. The minimum oxygen concentration in a gel capsule surrounding an embryo is preferably at least adequate to support enough growth of the radical (embryonic structure that eventually becomes the plant root) for it to rupture the capsule and become exposed to oxygen in the atmosphere. The radical is very sensitive to oxygen concentration. For example, if the oxygen concentration is too low, the radical dies before the radical can grow out of the capsule (see Example 2). Generally, if the oxygen concentration is high enough for growth of the radical, it is also high enough to support protrusive growth of other parts of the plant embryo from the capsule, such as the shoot. The minimum concentration of oxygen seems to depend in part on the particular plant species represented by the embryo. Other determinants of the concentration of oxygen in a gel can include the thickness of the gel, the fact that different types of gel solutes will absorb different amounts of oxygen, the degree of hydration of the gel, the concentration of the gel solute, presence or absence of other solutes in the gel such as nutrients and concentrations thereof, the temperature of the gel, and the presence or absence of an outer shell. Therefore, in most cases, the minimum oxygen concentration is best determined for a specific plant embryo and capsule configuration by performing a simple germination experiment involving a series of identically encapsulated embryos in which each gel capsule in the series has a stepwise different oxygen concentration from all other capsules in the series.

In a preferred embodiment, the concentration and availability of oxygen in the gel are increased by including in the gel an oxygen-absorbing or oxygen-carrying compound. Certain such compounds are so efficient at absorbing oxygen from the atmosphere that oxygenating the gel using oxygen gas is not necessary in some instances.

A preferred class of compounds for use in increasing the concentration of oxygen in a gel are the perfluorocarbons (PFCs). These compounds are organic compounds in which all hydrogen atoms have been replaced by fluorine atoms. They are nonpolar, colorless, odorless, non-toxic, heat-stable, and extremely chemically inert. Because gases Such as carbon dioxide and oxygen have a high solubility in PFCs, PFC compounds have been studied for use as blood substitutes. A first representative group of suitable PFCs comprises the perfluorocycloalkanes and perfluoro (alkylcycloalkanes) such as perfluorodecalin. A second representative group comprises the perfluoro(alkylsaturated heterocyclic) compounds such as perfluorobutyltetrahydrofuran. A third representative group comprises the perfluoro (tert-amine) compounds such as perfluorotributylamine.

Because PFCs are nonpolar, they are not miscible with aqueous liquids such as gel solutions. In order to combine a sufficient amount of a PFC with an aqueous gel solution to be useful as an oxygen absorber or carrier, it is necessary to create a suitably stable emulsion of the PFC. In such an emulsion, microdroplets of the PFC, comprising the disperse phase, are uniformly suspended in the gel solution (the continuous phase). As used herein, a "suitably stable" emulsion is one in which the disperse phase remains suspended in the continuous phase at least until the embryo has germinated from the capsule. To suitably stabilize the emulsion, a surfactant can be utilized. The emulsion can also be suitably stabilized in some instances merely by curing the gel.

The emulsion microdroplets are created by various methods known in the art, including using a high-shear mixing apparatus or via ultrasonic means. In the case of high-shear mixers, generally the higher the shear force imparted to the liquid mixture, the smaller the microdroplet size. In the case of ultrasonic devices, more ultrasonic energy must be pumped into the liquid mixture to achieve smaller microdroplet sizes. Representative ranges of microdroplet sizes are from about 100 μm diameter to less than 1 μm. In general, the smaller the microdroplet size, the more efficient the oxygen absorption and transport through the gel, since suspensions of smaller microdroplets have a larger total microdroplet surface area than suspensions of larger microdroplets. However, as a result of their greater surface area, suspensions of smaller microdroplets require more surfactant to render them suitably stable than emulsions of larger microdroplets.

Generally, the PFC concentration in a gel is about 25% w/v or less. The preferred concentration range of PFC in a gel is up to about 15% w/v. The optimal range will depend in part on the type of gel solute, the oxygen-carrying capability of the particular PFC, the size of the emulsion microdroplets, and the desired oxygen concentration in the gel. For example, the optimal concentration range of PFC in an emulsion with sodium alginate is within a range of about 7.5% w/v to about 12% w/v. Results of experiments investigating various levels of PFC and gel concentration can be found in the Examples.

Although a number of different types of surfactants would be effective in stabilizing an emulsion of PFC, the surfactant must be non-toxic to the embryo. As a result, certain ionic surfactants, such as sodium dodecyl sulfate, which easily disrupt cell membranes, are unsuitable (see Example 8). Other surfactants, such as egg albumin and non-ionic surfactants such as the methyl oxirane polymers (poly(oxyethylene)poly(oxypropylene) block copolymers) work well. An example is Pluronic F-68 from BASF Corp., Parsippany, N.J. In general, any substantially non-phytotoxic surfactant or emulsifier usable for food or ingestible pharmaceutical use would be satisfactory.

The maximum amount of surfactant required to achieve a suitably stabilized emulsion is generally about 10% w/v, but can be higher if extremely small microdroplets of PFC are formed during emulsification. In other words, as the diameter of microdroplets in a unit volume of PFC emulsion is decreased, the surface area of the PFC disperse phase is increased, and a correspondingly greater amount of surfactant is required to suitably stabilize the emulsion. The preferred range of surfactant concentration is from about 0.4% w/v to about 6% w/v. The surfactant is typically dissolved in water and PFC is added to the surfactant solution just before creating the emulsion. The emulsion is then combined with the uncured gel/nutrient solution. The resulting mixture is used to form the "artificial gametophyte."

An alternative oxygen-absorbing compound that can be incorporated as an emulsion into a hydrated gel is a silicone oil. Silicone oils are available in a number of viscosity values, where oils having a viscosity within the range of about 0.65 to about 15 centipoise are preferred. These oils, like PFCs, are nonpolar, colorless, odorless, non-toxic, heat-stable, chemically inert, and have high oxygen solubility values. In fact, some silicone oils have higher oxygen solubilities than many PFCs. Preparing an artificial gametophyte containing silicone oil is performed in substantially the same way as preparing an artificial gametophyte containing PFC. As with PFCs, a surfactant is generally required to achieve a suitably stable emulsion of silicone oil. Also, the concentration of silicone oil in a gel is generally about 25% w/v or less.

EMBODIMENTS OF FIGS. 1–3

After preparing the gel liquid, whether it includes emulsified PFC or silicone oil or not, preparing units of cured gel for use in germinating plant embryos can be done in a number of ways. The method chosen will depend in part upon how the embryo will contact the gel. It is important that the embryo have contact with the gel, either directly or via an intervening water-permeable "bridge" such as filter paper. In general, the embryo can rest on a surface of an oxygenated gel, rest in a preformed hole or cavity in a block of gel, or be entirely encapsulated in the gel. In the first two methods, the gel is generally cured preformed into the preferred shape, or can be formed as a larger cured mass and cut to size before inserting the embryo. In the case of totally encapsulating an embryo in the gel, it is preferable to insert the embryo in a unit of gel having the desired volume before the gel is completely cured.

FIG. 1A is a cross-sectional view of one embodiment of a seed analog 10 made by totally encapsulating an embryo 12 in a hydrated oxygenated gel capsule 14. One way to make such a capsule is to place the uncured gel mixture in a separatory funnel. The stopcock on the funnel is adjusted to form drops of the gel liquid in a slow stepwise manner. Whenever a drop forms at the tip of the separatory funnel, an embryo is inserted fully into the drop using sterile forceps. Then, the drop containing the embryo is either captured in a space conforming to the desired shape of the capsule for curing or, in the case of gels that must be complexed to cure, dropped into complexing solution until curing is complete.

Figure 1B:
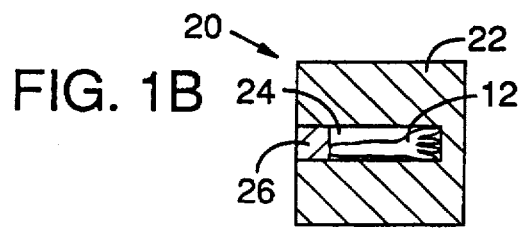
FIG. 1B is a cross-sectional view of an alternative embodiment of the analog of botanic seed shown in FIG. 1A.

FIG. 1B is a cross-sectional view of another embodiment of a seed analog 20 wherein a large portion 22 of the gel capsule is preformed. In FIG. 1B, the large portion 22 is shown in the shape of a cube, although other shapes will also suffice, such as spherical or ovoid. The larger portion 22 has a bore 24, which can also be preformed or cut after forming, into which the embryo 12 is inserted. If desired, the bore 24 can be sealed with a plug 26 after inserting the embryo 12. The plug 26 can be made of an additional piece of cured gel or other suitable material such as paraffin or similar material.

Figure 1C:
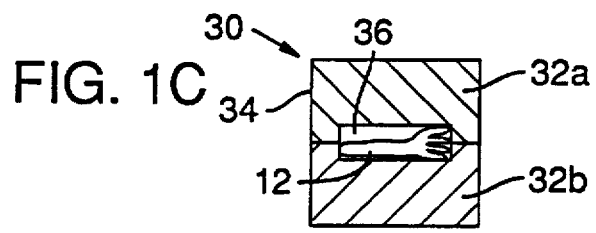
FIG. 1C is a cross-sectional view of another alternative embodiment of the analog of botanic seed shown in FIG. 1A.

As can be seen in FIG. 1C, yet another embodiment of a seed analog 30 according to the present invention can be made by preforming two opposing capsule halves 32a, 32b which, when pressed together to form a complete capsule 34, define a cavity 36 for receiving the embryo 12. Again, although FIG. 1C shows a cubic configuration, the general concept shown therein is adaptable to a variety of shapes.

It will be appreciated that variations on each of the three embodiments shown in FIGS. 1A, 1B, and 1C can be made which are within the scope of an encapsulated embryo according to the present invention.

It will also be appreciated that the embodiments of FIGS. 1A, 1B, and 1C can be made via an automated process.

Figure 2A:
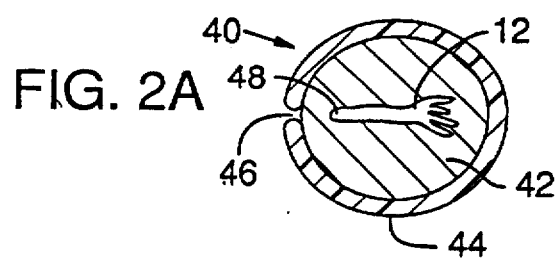
FIG. 2A is a cross-sectional view of an analog of botanic seed similar to that shown in FIG. 1A but also including an outer shell.

It is also possible to encase a gel-encapsulated embryo in a rigid shell to protect the gel capsule and embryo from physical injury, desiccation, and other adverse environmental forces. For example, FIG. 2A shows a cross-sectional view of one possible embodiment of such a seed analog 40 comprising an embryo 12, a capsule 42 comprised of a hydrated oxygenated gel in surrounding relationship to the embryo 12, and an outer shell 44 in surrounding relationship to the gel capsule 42. The outer shell 44 can be made from a large variety of materials including, but not limited to, a cellulosic material, paraffin, moldable plastic or cured polymeric resin, or a combination of these and/or other materials characterized by non-toxicity and suitable rigidity. However, the rigidity must not be such that an embryo germinating from within would not be capable of growing out of the seed analog 40 without fatal or debilitating injury. Hence, polymeric materials having a high dry strength and low wet strength are particularly desirable. Also desirable are shell materials that break apart easily upon application of an outwardly protrusive force from inside the capsule but are relatively resistant to compressive forces applied to the outside of the capsule. The outer shell 44 preferably also has an opening 46 toward which the radical 48 of the embryo 12 is oriented so as to facilitate protrusive growth of the radical 48 from the analog 40 during germination. Otherwise, the radical could become trapped inside the analog 40 and be prevented from successfully germinating.

Figure 2B:
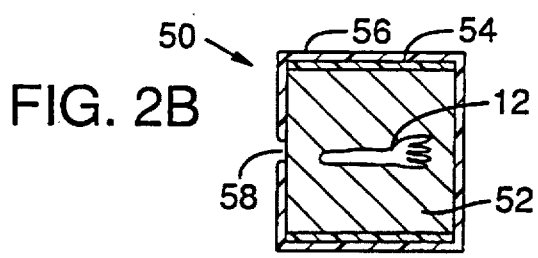
FIG. 2B is a cross-sectional view of an alternative embodiment of the analog of botanic seed shown in FIG. 2A.

Another possible embodiment is illustrated in FIG. 2B showing a cross-sectional view of a seed analog 50. The analog 50 comprises an embryo 12 and a capsule 52 comprised of a hydrated oxygenated gel in surrounding relationship to the embryo 12, where the capsule 52 is cast in an inner shell 54 to create a particular shape, such as a cylinder. The inner shell 54 can be cut, for example, from a plastic or cellulosic drinking straw or analogous material such as glass tubing. Then, the capsule-containing inner shell 54 is coated or otherwise layered with an outer shell 56 similar to the outer shell 44 of FIG. 2A. Again, it is preferable that the outer shell 56 include an opening 58 to ease protrusion of the germinating radical. It is also preferable that the outer shell 56 have a low wet strength and a high dry strength.

Figure 2C:
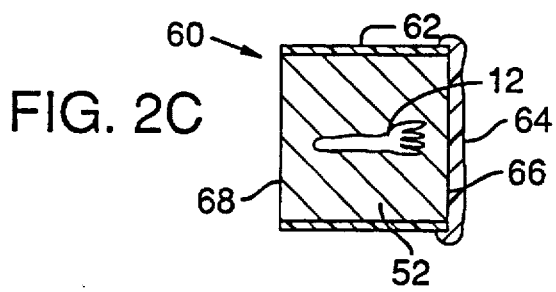
FIG. 2C is a cross-sectional view of another alternative embodiment of the analog of botanic seed shown in FIG. 2A.

Yet another possible embodiment of a shell-encased embryo-containing gel capsule is illustrated in FIG. 2C showing a cross-sectional view of a seed analog 60. As in FIG. 2B, the FIG. 2C embodiment comprises an embryo 12, a capsule 52 comprised of a hydrated oxygenated gel in surrounding relationship to the embryo 12, and a rigid cylindrical shell 62 similar to the inner shell 54 of FIG. 2B. In addition, a cap 64 of paraffin or other polymeric material is applied to at least the first end 66 to afford protection against desiccation and physical trauma as well as to properly restrain the cotyledons to facilitate normal germination. A second cap (not shown) similar to the first cap 64 can also be applied to the second end 68 for additional protection. If the shell 62 is made from a water-impermeable substance, it is preferable that the cap 64, especially if applied to both ends 66, 68, be made from a water-permeable substance to ensure adequate water penetration to the embryo 12 to support germination.

In all the embodiments shown in FIGS. 1A-1C and FIGS. 2A-2C, the hydrate oxygenated gel preferably includes dissolved nutrients. In addition, for oxygenation, the gel preferably includes a suitably stabilized emulsion of an oxygen-absorbing or oxygen-carrier substance such as a PFC compound or silicone oil suspended therein. In most instances, a gel containing such an emulsion should be oxygenated by passing oxygen gas through the gel before curing or afterward by exposure to oxygen gas after curing. Alternatively, at least for embryos of plant species requiring relatively low oxygen concentrations for germination, the gel including such an emulsion would be able to absorb sufficient oxygen from the atmosphere to ensure a high rate of embryo germination without the need for an oxygen-charging step.

In addition, whenever an embryo-containing gel capsule is substantially surrounded by an outer shell, it is at least partially isolated from the atmosphere. As a result, the gel should contain an emulsion as described above and be oxygen-charged to ensure that a sufficient supply of oxygen is present in the gel to supply the needs of the embryo during germination. In this case, the rigid oxygen-impermeable shell retards the oxygen in the gel from escaping to the atmosphere.

The embodiments shown in FIGS. 1A-1C and FIGS. 2A-2C are merely representative examples of possible capsule geometries. Other geometries and capsule configurations are possible. For example, FIGS. 3A-3C show cross-sectional views of three further embodiments wherein the capsules are bullet-shaped. Although capsules having such a shape can be useful for mechanical sowing, that is not the principal intent of the bullet shape. Rather, a tapered "bullet" end of a capsule helps guide an embryonic radical germinating from within the capsule to grow toward the "bullet" apex for ease of escape from the capsule. As with natural seeds, the capsules can be sown in any orientation in a soil or the like without interfering with the normal geotropism of the radical.

FIG. 3A shows schematically a "shelf" capsule 70 comprising a block 71 of hydrated oxygenated gel which preferably contains a stable emulsion of PFC or silicone oil. The gel block 71 defines a shelf 72 on which is placed an embryo 12 having a radical 48 oriented toward the tapered first end 73 of the capsule 70. In addition, the capsule 70 is shown having an optional separate nutrient unit 74 in contact with the gel block 71 and containing plant nutrients. The nutrient unit 74 may have any of a number of possible forms, including a hydrated gel containing dissolved nutrients, a mass of microencapsulated nutrients, a mass of slowly-soluble nutrient compounds, and other possible embodiments. Alternatively (not shown), the gel block 71 could occupy a larger space in the capsule 70 and also include nutrients dispersed throughout the gel block 71, thereby obviating the need for a separate nutrient unit 74.

FIG. 3A also shows an outer shell 75 in surrounding relationship to the block 71 and nutrient unit 74 as well as the embryo 12. To permit use of commonly available materials as the outer shell 75, such as tubular materials, the outer shell 75 preferably has a circular transverse cross-section, giving the outer shell 75 a cylindrical shape with a tapered first end 73 and a second end 76. The outer shell 75 can be constructed of, for example, a cellulosic tubular material similar to a paper drinking straw. Other materials such as plastic are also suitable. The tapered first end 73 can be formed via radical crimps 77 or other constriction method to reduce the diameter of the outer shell 75 at the tapered first end 73. The second end 76 can be similarly tapered (not shown) or it can be shaped as shown as a transverse circular flat contiguous with the outer shell 75. The tapered first end 73 preferably terminates with an orifice 78 toward which the radical 48 is urged to grow by the tapered first end 73 during germination. If required, the orifice 78 can be occluded with a covering 79 comprised of a soft material such as paraffin or a material having a high dry strength and a low wet strength. Alternatively, the covering 79 can be comprised of a material that breaks apart easily upon application of a protrusive force from inside the capsule.

During sowing (not shown), the capsule 70 can be deposited in soil or analogous plank-growing medium in any orientation. In the instance where the covering 79 has a low wet strength, subsequent irrigation would moisten and soften the covering 79 and allow the radical 48 of the germinating embryo 12 to escape from the capsule 70 into the soil.

FIGS. 3B and 3C schematically show alternative embodiments of the capsule design shown in FIG. 3A. In FIG. 3B, an embryo 12 is fully embedded in a block 81 comprising a hydrated oxygenated gel. The gel block 81 preferably also comprises a suitably stabilized suspension of PFC or silicone oil. A separate nutrient-containing unit 84 is shown contacting the gel block 81. However, as in the FIG. 3A embodiment, the nutrients can be included in the gel block 81, which obviates the need for a separate nutrient unit 84. Surrounding the gel block 81 and the nutrient unit 84 is an outer shell 85 shaped similarly to the outer shell 75 of FIG. 3A. The radical 48 of the embryo 12 points toward the tapered first end 83 of the outer shell 85. The tapered first end 83 terminates with an orifice 88 which is shown lacking the covering 79 of FIG. 3A to further illustrate possible embodiment variations. The FIG. 3B embodiment is preferred over the FIG. 3A embodiment because the embryo is secured against losing contact with the gel block 81 by being fully encapsulated therein.

The FIG. 3C embodiment is similar to the FIG. 3B embodiment with respect to the bullet shape of the capsule 90, the nutrient unit 94, and the outer shell 95 having a tapered first end 93 which terminates with an orifice 98. However, the hydrated oxygenated gel block 91 in which the embryo 12 is embedded is shown as an ovoid shape rather than the cylindrical shape of the gel block 81 in FIG. The FIG. 3C embodiment illustrates that the embryo-containing gel block 91 can be formed separately instead of being cast in the outer shell as suggested in FIG. 3B. Again, for improved oxygenation, the gel block 91 preferably includes a suitably stable suspension of PFC or silicone oil. Also, the separate nutrient unit 94 can be eliminated by incorporating the nutrients into the gel comprising gel block 91.

In the interest of clarity, FIGS. 3A and 3B show the tapered first ends 73 and 83, respectively, located some distance away from the radical 48. However, it is preferable, as shown in FIG. 3C, that the tapered first end 93 be located as close as possible to the radical 48. This ensures that, during germination, the radical 48 has only a minimal distance to elongate inside the capsule 90 before being urged toward the orifice 98 by the tapered first end 93. Otherwise, geotropism of an elongating radical may cause the radical 48 to grow away from the tapered first end 93 and make it difficult for the tapered first end 93 to urge the radical to grow toward the orifice 98.

FIG. 3D shows the exterior of an alternative embodiment 90a of the capsule 90 of FIG. 3C having an outer shell 95a, a tapered first end 93a, and a second end 96a corresponding to similar features shown in FIG. 3C. In FIG. 3D, the tapered first end 93a has a flat crimp 99 rather than the bullet-shaped configuration shown in FIG. 3C. As in FIG. 3C, the embryo radical (not shown) inside the capsule 90a of FIG. 3D is oriented toward the tapered first end 93a, particularly toward an opening 98a left in the crimp 99.

Oxygenation of Seed Analogs Using Oxygen Gas

Figure 14:
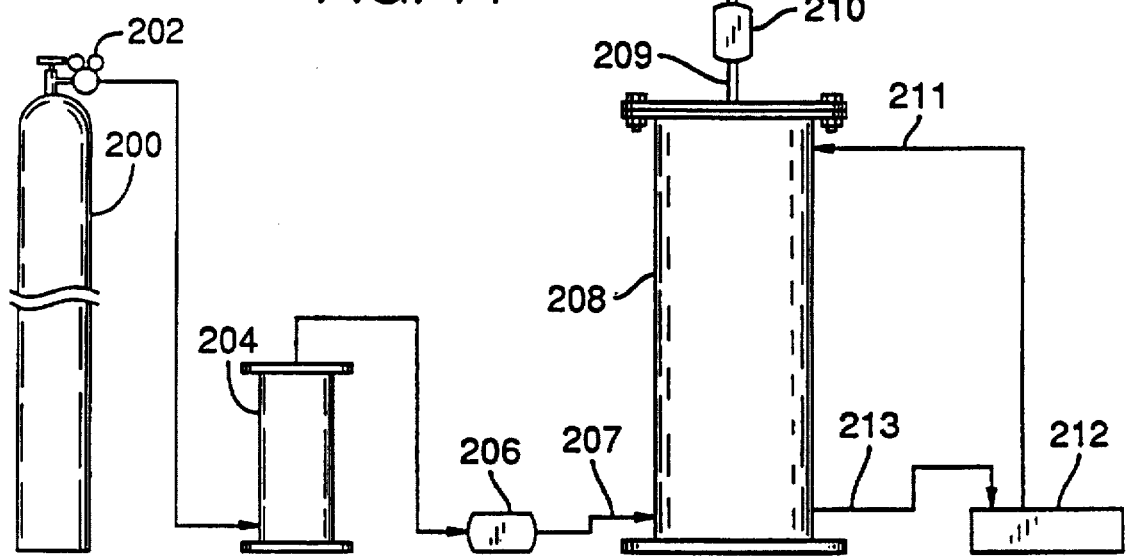
FIG. 14 is a plumbing diagram of a preferred embodiment of an apparatus for oxygenating seed analogs using oxygen gas.
Figure 15:
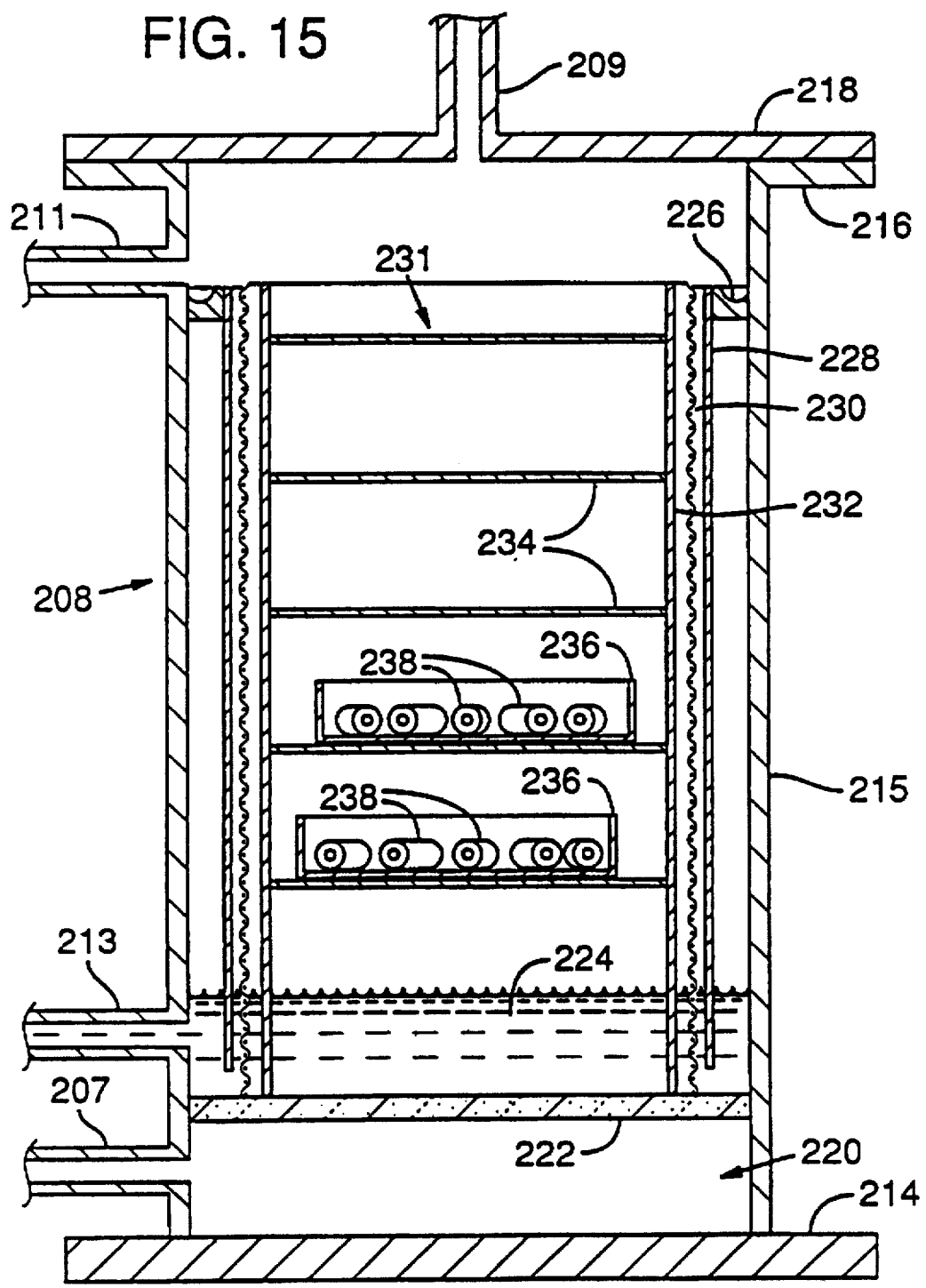
FIG. 15 is a sectional view of the interior of the oxygenation tower shown generally in FIG. 14.

A preferred embodiment of an apparatus for oxygenating seed analogs using oxygen gas is diagrammed in FIG. 14 and in detailed cross section in FIG. 15.

Referring to FIG. 14, pressurized oxygen from a supply 200 is directed through a regulator 202 to approximately atmospheric pressure. The oxygen is bubbled through water in a humidifier chamber 204 so that it is approximately saturated with vapor. The water-saturated oxygen is passed through a first biological filter 206 (having 0.2 mm-diameter pores) to remove entrained microorganisms. The oxygen then enters the base of an oxygenation tower 208 through an entry nipple 207. Seed analogs according to the present invention are placed inside the tower, as described below, to be oxygenated. The oxygen flows upward through the tower 208 and is discharged through a nipple 209 and a second biological filter 210. The second biological filter 210 ensures that microorganisms from the environment do not enter the tower 208 through the nipple 209. A closed-circuit flow of sterile water is maintained through the tower 208 by a pump 212. Water enters at the top of the tower 208 through a nipple 211 and is withdrawn at the bottom through a nipple 213. Saturating the oxygen with water vapor and maintaining water flow through the tower 208 creates an atmosphere inside the tower 208 nearly saturated with water, which prevents desiccation of the gel material and embryos in the seed analogs in the tower.

As shown in FIG. 15, a preferred embodiment of the tower 208 comprises a circular base member 214, an upright cylindrical portion 215 and a circular top flange 216. The tower 208 is capped by a removable circular cover 218 which may be appropriately gasketed and held in place by bolts or other means, not shown. The nipple 208 for discharging oxygen from the tower is located in the cover 218.

Internally, the tower comprises an oxygen entry plenum 220 at the bottom, served by the entry nipple 207. The entry plenum 220 is covered by a fritted metal or glass diffusion plate 222. A water reservoir 224 resides atop the diffusion plated 222 and drains through the nipple 213. A cylindrical porous curtain 228 extends downward from an annular gutter 226 to the reservoir 224. A removable rack 231, comprising vertical uprights 232 and horizontal shelves 234 for holding seed analogs 238, is adapted to fit inside the tower 208 and rest upright on the diffusion plate 222. A cylindrical member 230 made of woven metal screen or perforated sheet metal, situated between the curtain 228 and the rack 231, also rests on the diffusion plate 222.

Oxygen enters the plenum chamber 220 through the nipple 207. The oxygen passes through the diffusion plate 222 and bubbles through the water reservoir 224. Sterile water enters the tower 208 through the nipple 211 and flows into and fills the gutter 226. Water overflowing the gutter cascades down the curtain 228 into the reservoir 224. Water is withdrawn from the reservoir 224 through the nipple 213 for recirculation. The cylindrical member 230 surrounds the curtain 228 to prevent cascading water from splashing or dripping onto the rack 231.

During oxygenation thereof, seed analogs 238 according to the present invention can be placed directly on the shelves 234. If desired, the seed analogs 238 may also be placed in petri dishes 236 or other suitable tray to prevent the seed analogs from falling off the shelves 234. During oxygenation, the rack 231 (holding seed analogs 238) is placed inside the tower 208 which is sealed shut by the cover 218. Oxygen and water flow through the tower 208 as described above.

The time required to oxygenate the seed analogs 238 in the tower 208 is not particularly critical. Periods from 10 to 24 hours have proven satisfactory. The actual time required will depend somewhat on the construction of the seed analog, especially the amount of gel surface exposed to the atmosphere inside the tower. For example, seed analogs of the types shown in FIGS. 1A, 1B, or 1C might require less oxygenation time than those of FIGS. 2A, 2B, or 16. Little advantage has normally been seen when oxygenation periods exceed about 18 hours.

Germination From Seed Analogs Having Oxygenated Gels

Figure 4:
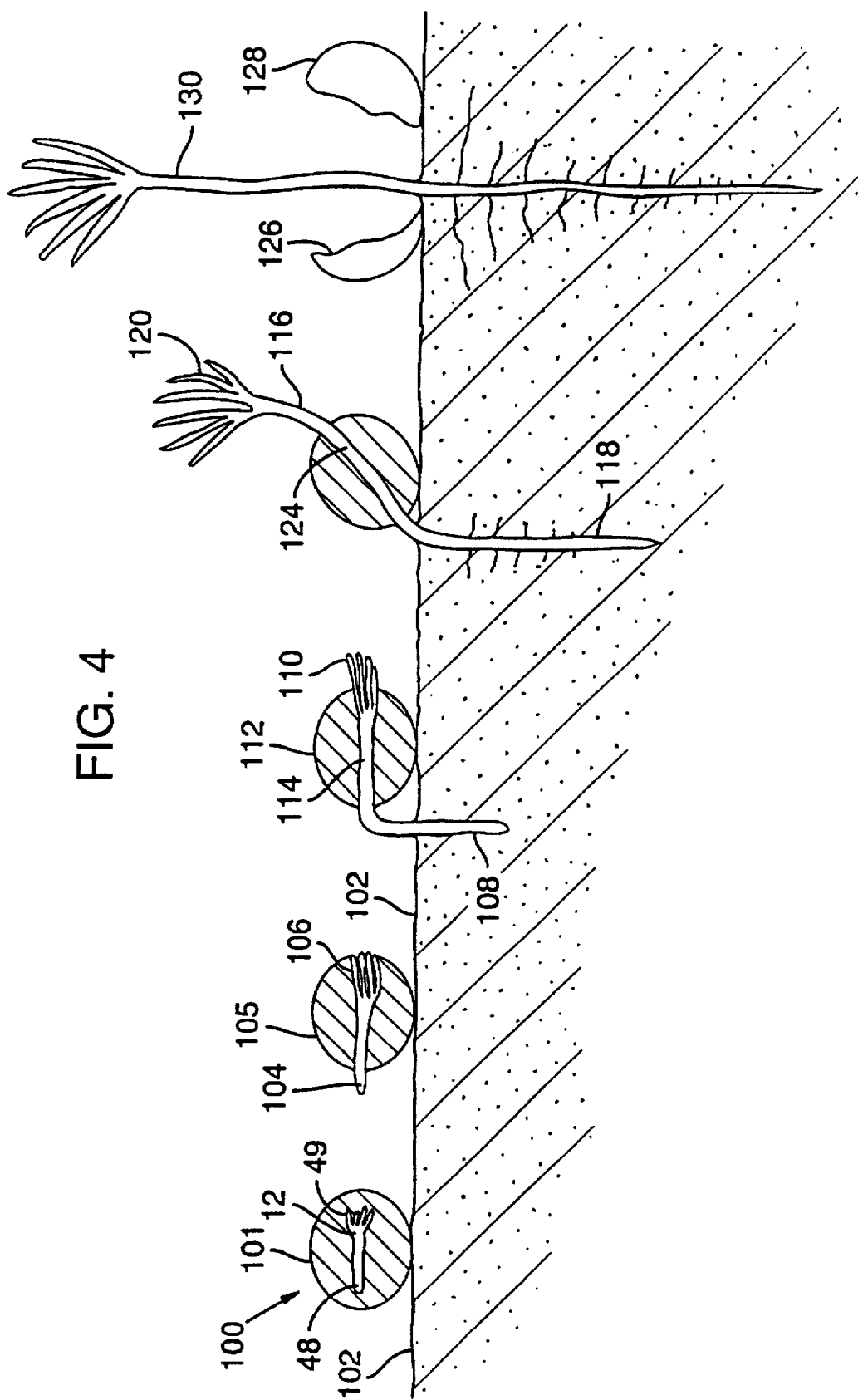
FIG. 4 is a stepwise sequential diagram illustrating one form of germination pattern frequently observed with an analog of botanic seed according to the present invention, wherein the gel capsule remains attached for a time to the hypocotyl of the germinating embryo.

FIGS. 4 and 5 each show stepwise sequential images of a gymnosperm embryo 12 germinating from an analog of botanic seed 100. Although the analog 100 is shown comprising an ovoid-shaped hydrated oxygenated gel capsule 101, it will be appreciated that FIGS. 4 and 5 are also applicable to other capsule embodiments, such as those including an outer shell. For simplicity, the seed analog 100 is shown being "sown" by placing on top of a soil surface 102, even though in most cases the analog 100 would be sown beneath the soil surface 102. Also, for clarity, each image except the rightmost image in each of FIGS. 4 and 5 is shown as a cross-sectional view.

FIG. 4 shows a stepwise germination sequence of an embryo 12 from the capsule 101 in which both the radical 48 and the cotyledons 49 burst from different ends of the capsule 101 at substantially the same time. The first, or leftmost, image shows the capsule 101 containing an embryo 12 embedded therein. In the second image, germination has begun and the growing radical 104 has undergone sufficient growth to burst out of the capsule 105. Also, the cotyledons 106 have undergone sufficient growth to just begin protruding from the capsule 105. In the third, or middle, image, a root 108 (which developed from the radical) is shown penetrating the surface 102 of the soil, and the cotyledons 110 have further elongated. The capsule 112 thus remains affixed to the hypocotyl 114 in a manner similar to bead on a string. In the fourth image, the seedling 116 has become more upright, the root 118 has grown longer downward and the cotyledons 120 have begun to spread apart. The capsule 122, however, remains attached to the hypocotyl 124. Finally, in the rightmost image of FIG. 4, the capsule is shown having split into two halves 126 and 128 and fallen off the seedling 130.

For purposes of comparison, FIG. 5 shows a germination pattern closely resembling that of a natural seed, wherein the seed analog 100 exhibits a degree of cotyledon restraint that simulates a normal botanic seed. In the first, or leftmost, image, the analog of botanic seed 100 is comprised of an embryo 12, having a radical 48 and cotyledons 49, and a hydrogenated oxygenated gel capsule 101 in surrounding relationship to the embryo 12. In the second image, the radical 132 has burst from the capsule 134. In the third image, a root 136 is shown penetrating the soil surface 102 and the cotyledons 138 have elongated. The capsule 140 is adapted to have sufficient strength to restrain the cotyledons 138 from growing into and becoming entrapped in the capsule 140 as the cotyledons elongate, thereby allowing the capsule 140 to be pushed ahead of the growing cotyledons 138. In the fourth image, the root 142 and cotyledons 144 have grown longer. The capsule 146 remains attached to the cotyledons 144 while allowing them to elongate naturally without malforming or becoming entrapped. In the fifth image, the seedling 148 has elongated sufficiently to elevate the capsule 150 off the soil surface 102. Finally, in the rightmost image, the capsule 152 has fallen off the cotyledons 154 in a manner similar to a seed husk of a natural seed. The seedling 156 appears normal and has excellent prospects for future growth.

In the Examples below, a growth pattern such as that shown in FIG. 4 wherein the capsule remains adhered to the hypocotyl of a germinated embryo for a time is regarded as not as desirable as that shown in FIG. 5 wherein the capsule temporarily restrains the cotyledons in a manner similar to a natural seed. Nevertheless, there is no evidence that a germination pattern as in FIG. 4 is in any way detrimental to the survival of the seedling. The germination patterns discussed above in relation to FIGS. 4 and 5 have been regularly observed during numerous studies of various embodiments of analogs of botanic seed according to the present invention. While the pattern of FIG. 5 more closely resembles that of a germinating natural seed, both the FIG. 4 and FIG. 5 patterns will result in production of normal seedlings.

Cotyledon Restraint

We have found that seed analog configurations allowing the developing cotyledons and/or epicotyl to become entrapped within the artificial gametophyte are not preferred. Such entrapment can prevent the growing plant from emerging from the seed analog, thereby causing abnormal growth and even death of the germinating embryo. Hence, as disclosed in further detail in Example 14, a seed analog allowing "natural" emergence of the germinating embryo and ultimate shedding of the capsule is most preferred.

Figure 16:
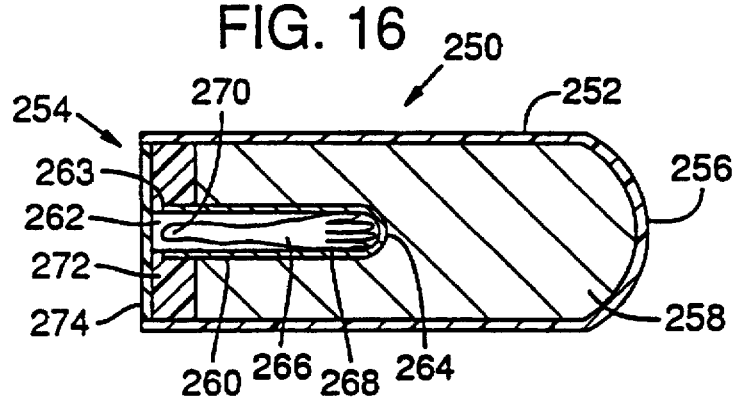
FIG. 16 is a sectional view of a preferred embodiment of a seed analog with provision for cotyledon restraint.

A most preferred embodiment for a seed analog offering cotyledon restraint according to the present invention is shown in FIG. 16, wherein a seed analog 250 comprises an outer shell 252 substantially surrounding a nutritive gel 258 which serves as an artificial gametophyte for the embryo 266. The outer shell facilitates the maintenance of elevated oxygen levels within the seed analog 250 while allowing the germinant that develops from the embryo 266 to escape from the seed analog during germination.

The outer shell 252 has an open end 254 and a closed end 256. The outer shell 252 can be constructed of a thin plastic material or a cellulosic material that has been made water resistant by such means as dipping in a suitable liquid hot wax such as melted paraffin. The outer shell 252, if used, may contain chemical additives such as antibiotics and/or fungicides to control possible invasion by microorganisms from the external environment. One way to fabricate the outer shell 252 that has proven very satisfactory is to fashion the outer shell from a portion of a common paper soda straw about 6.5 mm in diameter and 10–20 mm long. An outer shell 252 made of cellulose or other readily biodegradable material is preferred so that nursery beds will not be cluttered with spent shells from previous crops. The closed end 256 may be created by the use of a suitable plug or barrier or preferably simply by crimping to form a somewhat dome-shaped or conical end. An outer shell 14 to 18 mm long length will hold about 0.8 mL of gel. A volume of gel from 0.5 to about 1.0 mL is usually very satisfactory.

The nutritive gel 258 can be any of the types of gels discussed hereinabove, optionally comprising nutrients and oxygen carriers. A preferred gel 258 is agar-based because agar will gel (i.e., "set" or "cure") spontaneously by lowering the temperature. The gel 258 should be somewhat firm to prevent seepage of liquid from the gel into the cavity 262 containing the embryo. Flooding of the cavity 262 can cause low percentage of normal germinants. An agar concentration of about 1.8 g/L has proved to be very satisfactory.

The size of the outer shell 252 can vary, depending upon the species of plant being propagated. The dimensions and gel capacities recited above are suitable for propagation of Douglas-fir embryos and should not be considered limiting for this or other species.

The embryo 266 is contained within an inner porous tube 260 to provide, at least in part, sufficient cotyledon restraint. The inner porous tube 260 has an open end 263 and a closed end 264. The embryo 266 is situated within the seed analog 250 so that the cotyledons 268 are oriented toward the closed end 264 and the latent radical 270 is oriented toward the open end 263. The porous tube 260 may be made of various materials that are not phytotoxic and permit adequate transfer of moisture and nutrients to the embryo 266. Porous materials such as, but not limited to, filter paper, plaster of paris, and reasonably rigid open celled foams have all proved satisfactory. (Further details on forming the porous tube are provided hereinbelow.) A porous tube made from filter paper or similar material may optionally contain small perforations. For Douglas-fir somatic embryos a porous-tube length of 4 to 8 mm and an internal diameter of about 1.5 to 3 mm has proven very satisfactory. The internal diameter of the porous tube 260 should be sufficient to allow a somewhat enlarged cotyledon portion 268 of the embryo to be in intimate contact with the walls of the porous tube 260. Nutrients from the oxygenated gel pass through the porous tube 260 and are apparently absorbed by the growing embryo through the cotyledons. As stated above, the gel 258 should be firm enough to prevent excess liquid from seeping from the gel 258 into the cavity 262 occupied by the embryo 266.

The outer shell 252 may be filled with nutrient gel 258 by any of a number of means described hereinabove. A preferred method is by use of an automated pipette. Each outer shell 252 is filled to within a few millimeters of the open end-254 and the gel 258 allowed to set by cooling (if agar is used) or by ion exchange (if sodium alginate is used).

A coaxial internal cavity is formed in the gel 258 to accept the porous tube 260. The cavity can be molded in the gel as the gel sets or formed after the gel has set. Forming the cavity after the gel sets may be performed in a number of ways. For example, a thin-walled cylindrical steel tube used as a punch has proved very suitable. The gel core left within the steel tube can be readily removed-by application of vacuum. The cavity thus formed in the gel should have an internal diameter about equal to the outside diameter of the porous tube 260 so that intimate contact therebetween is maintained. The porous tube 260 may be inserted into the cavity by use of a mandrel. Preferably, a porous tube 260 inserted into the cavity is prewetted with water to avoid withdrawing water from the gel. Alternatively, the porous tube can be formed inside the cavity, as described in further detail below.

After forming or inserting the porous tube 260 in the cavity, the embryo 266 can be inserted into the porous tube 260 cotyledon-end first.

After insertion of the embryo 266, the seed analog 250 can be oxygenated as described previously. We have found that oxygenation following embryo insertion is preferable to preoxygenation of the gel from the standpoint of automation, although the results are essentially the same.

Following oxygenation, a primary end seal 272 is applied over the gel surface and around the protruding open end 263 of the porous tube 260. However, the primary end seal 272 should not cover the open end 263 of the porous tube 260. This result can be readily achieved by inserting an appropriate mandrel in the end of porous tube 260 while the primary end seal 272 is being formed.

Many materials are suitable for the primary end seal 272. Ordinary paraffin wax has proved very satisfactory. The primary end seal 272 is typically 2 to 4 mm thick but this is not in any way critical.

Preferably, a secondary end seal 274 is applied over the primary end seal 272 so as to cover the open end 263 of the porous tube 260. The secondary end seal 274 should be very thin, most typically no more than about 1 mm thick. It may be made of the same material as the primary end seal 272. For example, one way to form the secondary end seal 274 is to heat the surface of the primary end seal 272 sufficiently to cause surface melting thereof and draw a small amount of the molten material cross the open end 263 so as to form a film over the open end 263.

As with the outer shell 252, if one is used, pathogen-control chemicals may optionally be added to the primary and secondary end seals.

The closed end 264 on the porous tube 260 has been found to be advantageous. The closed end 264 prevents the cotyledons 268 growing inside the porous tube 260 from penetrating the porous tube and expanding into the gel 258. We have found that cotyledons 268 that expand into the gel 258 become entrapped in the gel in a manner that prevents the growing plant from escaping from the seed analog. Such entrapment is believed to be a significant cause of germinant abnormalities. The growing cotyledons are preferably only temporarily restrained within the porous tube 260. As they grow and elongate, the cotyledons bear against the internal surfaces of the porous tube and urge the cotyledons out of the porous tube and, consequently, out of the artificial gametophyte. In this regard, the FIG. 16 embodiment effectively simulates a natural seed.

It will be appreciated that manufacture of the FIG. 16 embodiment, as well as other embodiments disclosed herein, can be readily automated to eliminate hand labor.

Generally, appropriate cotyledon restraint can be achieved via a number of ways including, but not limited to, the following:

(1) Enclosing the embryo in a preformed cylinder that surroundingly contacts the embryo, wherein the cylinder is encapsulated in a nutrient gel ("artificial gametophyte"), as indicated generally in FIG. 16. As described above, the preformed cylinder should be porous and can be fabricated from suitable materials such as, but not limited to, glassy, metal, elastomeric, ceramic, clay, plaster, cement, starchy, putty-like, synthetic polymeric, natural polymeric, and adhesive materials.

(2) Forming a cavity in a gel capsule and attaching a porous material to the walls of the cavity before inserting an embryo into the cavity. Candidate porous materials include, but are not limited to, dialysis tubing, natural sausage casing material, paper, fabric, and collagen materials.

(3) Forming a first cavity in a gel capsule, filling the cavity with a conformable porous substance, then either forming a smaller-diameter second cavity in the porous substance coaxial with the first cavity before inserting an embryo into the second cavity, or inserting the embryo directly into the porous substance in the first cavity. Alternatively, at least the cotyledon end of the embryo is dipped in the conformable porous substance before the embryo is inserted in the first cavity. Representative conformable porous materials include, but are not limited to, plaster of paris, cement, natural and synthetic polymers, tree resins, porous waxes, agar or alginate at a higher concentration than used for the gel capsule, and clays.

(4) "Hardening" the gel itself, such as before or after forming a cavity therein, then inserting an embryo into the cavity. As used herein, "hardening" refers generally to making the gel comprising the artificial gametophyte stiffer or more rigid. Hardening can be effected by increasing the concentration of the gel, performing a "surface drying" of the gel, or by adding a particulate material to the gel. Candidate particulate materials include, but are not limited to, sand, plaster of paris, pulp fibers, cement, and polymeric substances.

(5) Inserting a sheet or piece of porous material between the embryo and the gel as the embryo is inserted into the gel. Candidate porous materials include, but are not limited to, paper, polymer-soaked paper, fabric, and polymer sheets.

(6) Forming a cavity in the gel, then applying a conformable porous coating on the walls of the cavity. Candidate coating materials include, but are not limited to, dry powdery materials such as plaster of paris or cement that, when wetted by liquid from the gel, form a porous barrier. Alternatively, a web-forming material can be applied to the walls of the core, such as gelatin powder, sponge material, natural webbing, and foams.

(7) Forming the gel capsule ("artificial gametophyte") using a sufficiently concentrated gel solution to prevent an embryo germinating therein from growing into and becoming entrapped in the gel.

Figure 17:
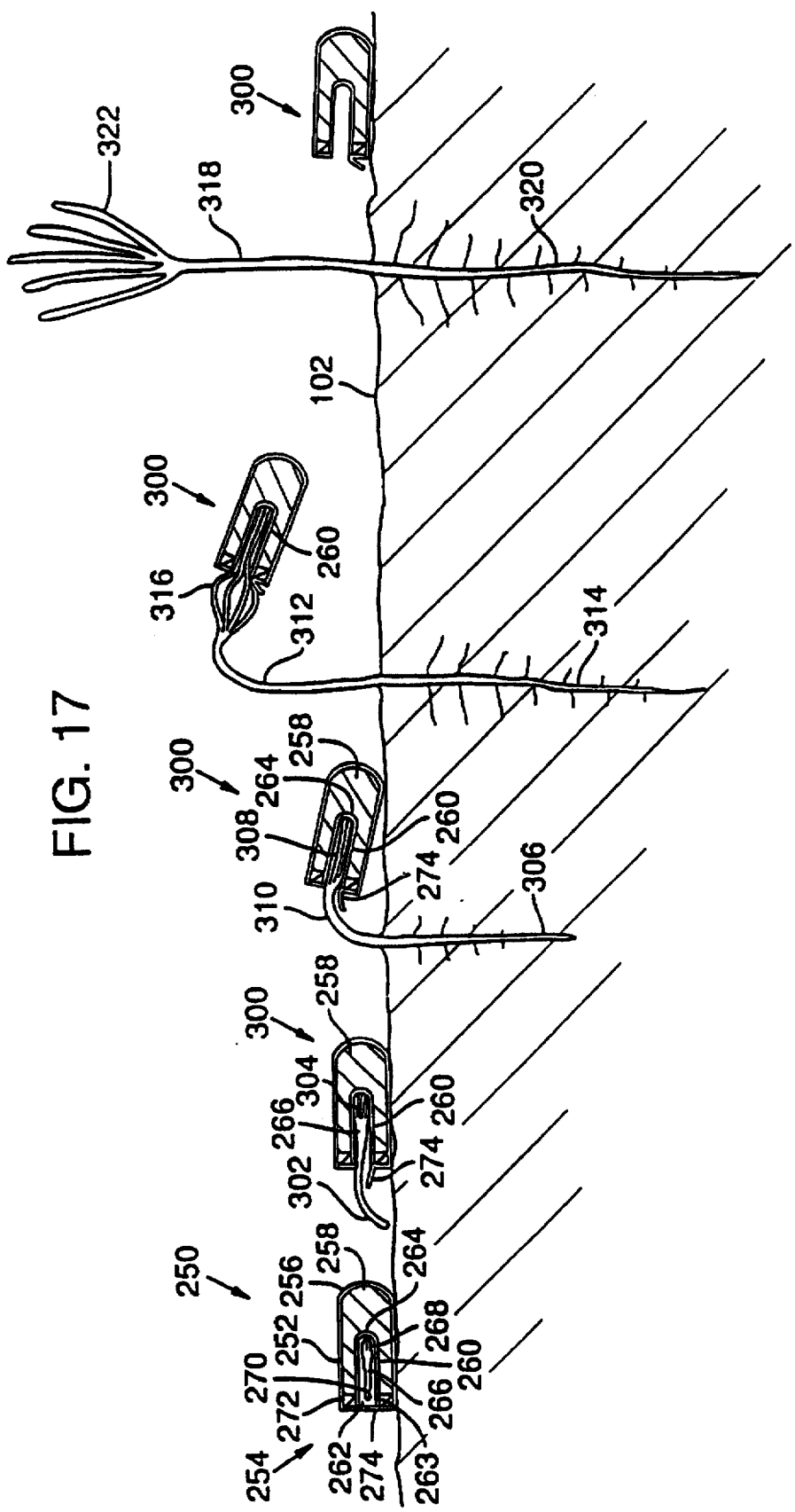
FIG. 17 is a stepwise sequential diagram illustrating germination of the FIG. 16 embodiment of a seed analog.

FIG. 17 shows a stepwise germination sequence, similar to FIGS. 4 and 5, of a gymnosperm embryo 266 from the FIG. 16 embodiment of a seed analog 250. The first, or leftmost, image shows the seed analog 250 resting on the surface 102 of soil or analogous plant growth. The analog 250 is shown, for simplicity, having been "sown" on the surface 102. However, it will be appreciated that the analog 250 can also be sown beneath the surface 102. In the leftmost image, reference designators are identical to those used in FIG. 16.

In the second image from the left, germination has begun and the growing radical 302 has undergone sufficient growth to burst open the secondary end seal 274. Thus, the radical 302 begins to grow outward and downward from the capsule 300 so as to eventually form a root anchoring the germinant in the soil. At the onset of germination, before the embryo 266 bursts from the seed analog 250, nutrients (if any), oxygen and other gases, and water in the gel 258 ("artificial gametophyte") pass from the gel 258 through the porous tube 260 to be absorbed by the embryo 266. Immediately after the growing radical 302 has burst open the secondary end seal 274, atmospheric oxygen can enter the cavity 262 to supplement oxygen supplied by the gel 258 to the embryo 266. It can also be seen in the second image that the cotyledons 304 have begun to enlarge and elongate, whereupon they bear against the inside walls of the porous tube 260 to facilitate escape of the radical 302 from the capsule 300.

In the middle image of FIG. 17, the radical has further elongated and entered the soil to form a root 306. The cotyledons 308 have further elongated and are continuing to bear against the inside walls of the porous tube 260, including the closed end 264 of the porous tube, thereby further facilitating a "natural" germination. The porous tube 260 allows continued transfer of nutrients (if any), water, oxygen, and other gases from the gel 258 to the germinant 310 while preventing the cotyledons 308 growing within the tube 260 from penetrating the tube 260. Thus, the cotyledons 308 are prevented from becoming entrapped in the gel 258.

In the fourth image from the left in FIG. 17, the germinant 312 has further grown to have a longer root 314 and (although not always the case) lift the capsule 300 off the surface 102. The cotyledons assume a natural "birdcage" appearance as they further elongate out of the porous tube 260.

Finally, in the rightmost image, the germinant 318 has become fully upright and has shed the capsule 300 in a manner analogous to the natural shedding of the remains of a botanic seed by-a healthy germinant therefrom. The root 320 has continued to grow downward and the cotyledons 322 have spread apart. The germinant 318 has excellent prospects for developing into a healthy plant.

Further Definitions

The following terms as used in the Examples are defined as follows:

"Somatic embryo" is a plant embryo that developed via the laboratory culturing of totipotent plant cells or by induced cleavage polyembryony.

"Zygotic embryo" is a plant embryo removed from a seed of the corresponding plant.

"Germinant" is an embryo that has undergone sufficient growth and development to protrude from a capsule, analogous to protruding from a natural botanic seed.

"Radical" is that part of a plant embryo that develops into the primary root of the resulting plant.

"Cotyledon" refers generally to the first, first pair, or first whorl (depending on the plant type) of leaf-like structures on the plant embryo that function primarily to make food compounds in the seed available to the developing embryo but in some cases act as food storage or photosynthetic structures.

"Hypocotyl" is that portion of a plant embryo or seedling located below the cotyledons but above the radical.

"Epicotyl" is that portion of the plant developed after germination from the stem apex.

"Capsule" refers at least to a hydrated gel in surrounding relationship to a plant embryo embedded therein.

"Hypocotyl length" pertains to the length of the hypocotyl at the time the hypocotyl was measured.

"Hypocotyl germination" denotes the emergence of the embryo shoot from the capsule, caused by elongation of the hypocotyl sufficiently to burst the capsule. This term does not take into consideration any length criteria or lack of hypocotyl malformations.

"Swollen hypocotyl" is an attribute of an abnormal embryo characterized by the hypocotyl or a portion thereof having a greater than normal diameter compared with hypocotyls on control bare embryos grown on the surface of a nutrient agar or similar nutrient medium.

"Twisted hypocotyl" is an attribute of an abnormal embryo characterized by the hypocotyl having grooves spiraling longitudinally up or down the length of the hypocotyl. This defect is usually found only in embryos exhibiting swollen hypocotyls.

"Swollen cotyledons" is an attribute of an abnormal embryo of a gymnosperm characterized by unusually large cotyledon(s) compared to cotyledons on control bare embryos grown on the surface of a nutrient agar or similar nutrient medium.

"Twisted cotyledon" is an attribute of an abnormal embryo of a gymnosperm characterized by the cotyledon(s) having a spiraled or twisted appearance.

"Radical length" pertains to the length of the radical at the time the radical was measured.

"Radical germination" denotes the emergence or protrusive growth of the root from the capsule, caused by elongation of the radical sufficient to burst the capsule. This term does not take into consideration any length criteria.

"Growth through capsule" occurs when an embryo inside the capsule undergoes elongation both of the radical and the hypocotyl and bursts the capsule at both ends. This is usually evidenced by the capsule remaining for a period of time as a captive spherical body around the hypocotyl.

"Normalcy" denotes the presence of all parts (radical, hypocotyl, cotyledon(s), epicotyl) at time of evaluation, where, in the case of gymnosperms, the radical has length greater than 3 mm and no visibly discernable malformations compared to the appearance of control bare embryos grown on the surface of nutrient agar or similar nutrient medium.

It is important to note that, as long as all parts of an embryo have germinated, the corresponding germinant probably has the potential to become a normal seedling. We have no reason to believe that malformations evident in the following Examples below are fatal to germinants. Noting the quantity and quality of malformation is a convenient way to comparatively evaluate the various methods and means employed for making analogs of botanic seed. Fortunately, plant embryonic tissue is exquisitely sensitive to non-natural conditions and manifests that sensitivity in ways discernable to a trained observer.

EXAMPLE 1

This Example is an evaluation, for comparison purposes, of embryo germination from non-oxygenated capsules of the type as disclosed in European Patent Application No. 0,107, 141. (The European application referred to herein as EPA '141 claims priority under U.S. Ser. No. 06/433,688, filed on Oct. 12, 1982.) Individual sets of zygotic embryos of Norway Spruce were subjected to one of the following Treatments:

Treatment (1): "Control" wherein bare embryos were placed directly on the surface of nutrient agar in a manner known in the art.

Treatment (2): Embryos encapsulated in sodium alginate in the manner disclosed in EPA '141.

Treatment (3): Capsules lacking embryos were formed as disclosed in EPA '141, after which each capsule was cut in half, an embryo placed in the center thereof, and the capsule halves were pressed together around the embryo to seal the capsule around the embryo.

All Treatments were placed in covered Petri plates on the surface of nutrient agar medium (1% agar). Six embryos were placed in each plate and six replicate plates were prepared for each Treatment. All plates were placed in a 23° C. incubator under continuous filtered fluorescent light to stimulate germination. After 28 days, the plates were removed from the incubator and examined for quality and quantity of germinants.

Upon examination, it was found that whole capsules according to EPA '141 (Treatment (2)) did not allow the radical to elongate. Although the hypocotyls of Treatment (2) embryos usually elongated, they were malformed (twisted and swollen). These results indicate that the embryo must exert an excessive force injurious to the embryo in order to germinate from the EPA '141 capsule.

Embryos encapsulated by Treatment (3) split into halves under the protrusive force of the germinating embryo, usually in the first two weeks. However, the germinants still did not exhibit normal development. Nevertheless, a higher percent of the embryos receiving Treatment (3) germinated than observed with Treatment (2) embryos. Lack of normal development of Treatment (3) embryos was apparently not due to excessive restraint imparted by the capsule since the capsules were seen to split easily.

Of the "Control" embryos of Treatment (1), 75% showed normal germination. In contrast, of the Treatment (2) embryos, only 6% showed normal germination; and of the Treatment (3) embryos, only 14% showed normal germination. These results indicate that, although encapsulating embryos in a more easily ruptured alginate capsule (Treatment (3)) improved embryo germination, some other factor, such as lack of oxygen availability through an unruptured capsule, seems to be responsible for the poor embryo development seen with embryos encapsulated according to EPA '141, relative to bare embryos placed on nutrient agar having an unlimited exposure to oxygen.

EXAMPLE 2

This Example was an evaluation of whether the position of the embryo within a gel capsule was a significant factor in determining the success rate of embryo germination and normal development.

Individual sets of zygotic embryos of Norway Spruce were subjected to one of the following treatments:

Treatment (1): "Control" wherein bare embryos were placed directly on the surface of nutrient agar in a manner known in the art.

Treatment (2): Capsules lacking embryos were formed as an EPA '141, after which each capsule was cut in half, an embryo inserted therein with the radical end positioned relatively close to the outer surface of the capsule compared with the shoot, then the capsule halves were pressed together around the embryo to reseal.

Treatment (3): As in Treatment (3) of Example 1.

All Treatments were placed in covered Petri plates on the surface of nutrient agar medium. Six embryos were placed in each plate and six replicate plates were prepared for each Treatment. All plates were placed in a 23° C. incubator under continuous filtered fluorescent light to stimulate germination. After 28 days, the plates were removed from the incubator and examined for quality and quantity of germinants. Results are tabulated in Table I.

Table I

| Treatment | % Normal Germinants | Mean Length Hypocotyls | Mean Length Radicles |
| --- | --- | --- | --- |
| 1 (Control) | 81% | 1.26 cm | 1.44 cm |
| 2 (Offset) | 17% | 0.63 cm | 0.98 cm |
| 3 (Centered) | 8% | 0.62 cm | 0.72 cm |

The data in Table I indicate the following conclusions:

(a) Embryos encapsulated with radicles situated close to the capsule surface (Treatment (2)) yielded two times more normal germinants than embryos encapsulated in the center of a capsule (Treatment (3)). This indicates that minimizing the protrusive force that must be exerted by a germinating radical to burst from a capsule is beneficial to the germinating embryo.

(b) Although mean hypocotyl lengths were about equal for Treatments (2) and (3), radical length was longer for Treatment (2), indicating that conditions for radical growth were more favorable in Treatment (2).

(c) Poor radical elongation in Treatments (2) and (3) appears to be due to a limiting factor, such as low concentration of oxygen, prior to capsule splitting. In instances where the radical failed to elongate at all, a brownish mass of tissue formed on the radical resembling a callus, indicating probable death of cells comprising the radical tip. Although the capsules in Treatments (2) and (3) appeared to split easily during germination, they apparently did not split early enough to prevent tissue death. The fact that a larger percentage of radicles did elongate in Treatment (2) was probably due to a higher amount of oxygen getting to the radical due to the split in the capsule.

EXAMPLE 3

This Example was an evaluation of the effects on embryo germination of varying the amount of surface area of zygotic embryos exposed to air.

Individual sets of zygotic embryos of Norway Spruce were subjected to one of the following treatments:

Treatment (1): "Control" wherein bare embryos were placed on the surface of nutrient agar in a manner known in the art.

Treatment (2): Bare embryos placed on the surface of a nutrient medium comprising complexed alginate (1.5% alginate) instead of agar.

Treatment (3): Embryos centrally encapsulated in blocks of nutrient agar (0.8% agar); blocks then placed on the surface of nutrient agar.

Treatment (4): Embryos encapsulated in blocks of nutrient agar (0.8%) with radicles protruding from the block; blocks then placed on the surface of nutrient agar.

Treatment (5): Embryos encapsulated as in EPA '141 except that the alginate concentration was 1.5%, and a nutrient aqueous liquid containing dissolved nutrients as in "MS liquid" was used instead of water to dissolve the alginate; capsule diameter was about 3 mm; capsules then placed on the surface of nutrient agar.

To prepare alginate for Treatment (2), a 1.5% alginate solution was prepared using a nutrient liquid similar to "MS liquid" and poured slowly into sterile Petri dishes until the bottom of each dish was covered. A solution of $Ca(NO_3)_2$ in the nutrient liquid was then sprayed into the dishes using a plastic spray bottle to initiate complexing (gelling) of the alginate. After the alginate began to gel (about 3 minutes), more $Ca(NO_3)_2$ solution in nutrient liquid was poured into each dish to submerge the gelled alginate therein for about 20 minutes. The $Ca(NO_3)_2$ was then poured off and the complexed alginate rinsed with nutrient liquid for 5 minutes.

To prepare agar blocks for Treatments (3) and (4), blocks of nutrient-containing agar were cut measuring about 4×4×5 mm using a small spatula. Using sterile forceps, an embryo was inserted into each block, centered in the block for Treatment (3) and with the radical protruding outside the block for Treatment (4). Embryos were inserted into the blocks radicle-end first for Treatment (3) and cotyledon-end first for Treatment (4). With Treatment (4), about half the embryo length was left protruding from the agar block.

Bare embryos (Treatment (1)) and encapsulated embryos (Treatments (2)–(5)) were placed on nutrient-agar surfaces in Petri dishes. The dishes were covered and placed in a 23° C. incubator under continuous filtered fluorescent light for 35 days. Subsequent examination revealed the data shown in Table II.

Table II

| Treatment | % Normal Germinants | % Germinants w/ Swollen Hypocotyls | % Germinants w/ Swollen Cotyledons |
| --- | --- | --- | --- |
| 1 (Agar control) | 90% | 0% | 0% |
| 2 (Alginate control) | 8% | 36% | 0% |
| 3 | 0% | 91% | 47% |
| 4 | 61% | 37% | 26% |
| 5 | 20% | 75% | 3% |

The results and conclusions can be summarized as follows:

(a) The agar blocks with protruding radicles (Treatment (4)) produced 61% normal germinants with radical and hypocotyl lengths similar to corresponding lengths of control embryos. This indicates that lack of physical restraint, free exposure to oxygen, and a nutrient supply are important for optimal growth of the radical.

(b) The embryos encapsulated in alginate (Treatment (5)) produced only 20% normal germinants. Fifty-nine percent of the radicles and 97% of the hypocotyls germinated but 74% of the hypocotyls were swollen and therefore did not undergo normal development. This indicates that full encapsulation in alginate presents at least one environmental restraint to normal germination, such as lack of oxygen.

(c) Bare embryos placed on the surface of complexed alginate (Treatment (2)) had the same amount of embryonic tissue exposed to air as the control embryos placed on agar (Treatment (1)). Nevertheless, the Treatment (2) embryos experienced much less normal germination than controls. The reason for this is unclear.

(d) The embryos embedded completely inside nutrient agar blocks (Treatment (3)) therein yielded no normal germinants at all. All hypocotyls germinated but 92% thereof were swollen. This indicates, as in Treatment (5), that complete encapsulation without providing oxygen appears to present an environmental impediment to successful germination.

EXAMPLE 4

This Example is an evaluation of germination performance observed with embryos of Norway Spruce individually inserted halfway into blocks of nutrient agar medium versus embryos individually placed on the surface of a unit of nutrient gel medium, where each unit of the gel medium was then surrounded by a rigid protective "shell" made of either thin transparent plastic or glass.

Individual sets of zygotic embryos were subjected to one of the following Treatments:

Treatment (1): "Control" wherein bare zygotic embryos were placed on the surface of nutrient agar medium.

Treatment (2): As shown in FIG. 6, glass cylindrical capsule shells 160 were made having length about 12 mm, outside diameter about 7 mm, and inside diameter about 5.6 mm. One end 161 of each shell was sealed with an elastomeric septum 162. After sterilization, the shells were oriented vertically open-end up and filled about two-thirds full with nutrient agar medium 163. A zygotic embryo 164 was inserted halfway into the exposed agar surface 165 in each shell, cotyledon end 166 first, leaving the radical 167 exposed to the atmosphere. The resulting capsules 168 were turned on their sides on a nutrient agar surface for incubation.

Treatment (3): Same as Treatment (2) except that, after inserting the embryos in the agar, the open ends of the glass shells were subsequently partially sealed from the atmosphere using PARAFILM laboratory film (a registered trademark of American National Can, Greenwich, Connecticut). The film was applied to the open end in a manner that left a small hole through which the radical could protrude during germination.

Treatment (4): As shown in FIG. 7, rigid shells 170 were made by cutting a 4 mm diameter clear plastic drinking straw to 4 mm lengths. After sterilization, each shell 170 was oriented horizontally and filled about half full with nutrient agar medium 171, leaving a flat agar surface 172 inside each shell extending the length of the shell. An embryo 173 was placed on the agar surface (or "shelf") inside each shell. One end 174 of each shell was sealed using paraffin 175; the other end 176 was left open to the atmosphere, where the radical 177 of the embryo 173 therein pointed toward the open end 176. The resulting capsules 178 were placed on their sides on a nutrient agar surface for incubation.

Treatment (5): Same as Treatment (4) except that, after placing the embryo in the capsule, the open end of the shell was partially sealed using PARAFILM in the same manner as described in Treatment (3).

Treatment (6): As shown in FIG. 8, rigid shells 180 were made by cutting a 4 mm diameter clear plastic drinking straw to 8 mm lengths. After sterilization, each shell 180 was oriented horizontally and filled about half full with nutrient agar medium 181, leaving a flat agar surface 182 inside each shell extending the length of the shell. One end 183 of each shell was sealed by dipping to a depth of 4 mm in paraffin 184, thereby causing the paraffin 184 to occupy about half the air space inside the shell. An embryo 185 was placed on the agar surface 182 (or "shelf") inside each shell, with the radical 186 pointing toward the open end 187, which was left exposed to the atmosphere. The resulting capsules 188 were placed on their sides on a nutrient agar surface during germination.

Treatment (7): As in Treatment (6) except that, after placing an embryo on the "shelf" in each capsule, the open capsule ends were partially sealed using PARAFILM in the same manner as described in Treatment (3)

All Treatments were incubated in covered 100 mm diameter Petri plates for germination. Treatment (1) employed six plates containing six embryos each. Treatments (2) through (7) employed three plates each, six capsules per plate. The plates were incubated for 35 days under conditions as described in Example 1. Data are tabulated in Table III.

TABLE III

| Treatment | % Normal Germinants | % Swollen Hypocotyls | % Swollen Cotyledons | % Embryos Completely Trapped | % Cotyledons Trapped |
|---|---|---|---|---|---|
| 1 (Control) | 72% | 22% | 6% | 0% | 0% |
| 2 | 39% | 44% | 11% | 6% | 78% |
| 3 | 6% | 78% | 45% | 28% | 61% |
| 4 | 72% | 17% | 0% | 17% | 61% |
| 5 | 12% | 45% | 0% | 39% | 61% |
| 6 | 50% | 34% | 6% | 6% | 61% |
| 7 | 34% | 45% | 6% | 11% | 79% |

Conclusions based on Table III and other observations were summarized as follows:

(a) All Treatments lacking the PARAFILM-sealed end (Treatments (1), (2), (4), and (6)) exhibited a higher percent of normal germination, indicating a benefit of free exposure o the embryos to oxygen.

(b) Controls (Treatment (1)) as well as Treatment (4) exhibited the highest percentages of normal germinants (72%), followed by Treatment (6) at 50% and Treatment (2) at 39%. Apparently, the combination of light capsule weight and exposure of at least the radical to oxygen during germination was beneficial.

(c) No swollen cotyledons were seen in embryos that experienced Treatment (4) or Treatment (5), indicating a benefit of lightweight capsules.

(d) Treatments (3)–(6) exhibited the same percent of trapped cotyledons, even though the amount of medium in the capsules differed between Treatment (3), Treatments (4) and (5), and Treatment (6). Apparently, these capsule geometries are not optimal for allowing early release therefrom during gymnosperm germination.

(e) Partially sealing the radical-end of the capsules with PARAFILM resulted in lower average lengths of hypocotyls and radicles (data not shown), probably demonstrating a slight negative effect of partial (although not excessive) physical obstruction of the radical until it penetrated the opening in the PARAFILM.

(f) Treatment (4) embryos experienced the same percent normal germinants as the controls of Treatment (1). However, average lengths of hypocotyls and radicles, as well as average seedling weights (data not shown) of Treatment (4) embryos, were less than with control embryos. Such decreased values, however, probably merely reflect the slightly greater physical restraints placed on a Treatment (4) embryo versus a "bare" embryo when undergoing germination.

EXAMPLE 5

In this Example, we evaluated enclosing the embryo in a porous tube embedded in a nutrient-containing gel as an improved means for physically securing an embryo inside a gel capsule without actually embedding an embryo directly in the gel. This method was investigated because "shelf" capsules such as described in Treatment (4) of Example 4 generally cannot be turned or handled without the embryo falling off the gel "shelf." The capsules tested in this Example also included a rigid exterior shell for additional physical protection. Securing the embryo was performed using a tube made of filter paper, where the filter paper served as a liquid "bridge" between the gel and the embryo.

Individual sets of Norway Spruce embryos were subjected to one of the following Treatments:

Treatment (1): "Control" as in Treatment (1) of Example 4.

Treatment (2): As in Treatment (4) of Example 4.

Treatment (3): Glass shells having 5.2 mm inside diameter were made as described in Treatment (2) of Example 4. One end of each shell was sealed with an elastomeric septum, then the shells were sterilized. Each shell was then filled with nutrient agar. Small paper tubes having 2.5 mm inside diameter and about 5 mm long were made by cutting Whatman #1 qualitative filter paper into 5 mm-wide strips, each of which was rolled around a 2.5 mm outside diameter pin to form a paper tube. The tubes were kept from uncurling by application of a small piece of label tape (2×8 mm). The tubes were autoclaved and sealed on one end by dipping in hot paraffin. Each tube was axially inserted sealed-end first in an individual agar-containing glass shell until the open end of the tube was flush with the opening of the shell. An embryo was inserted in each paper tube cotyledon-end first until the radical tip was flush with the tube opening.

Treatment (4): Same as Treatment (3) except that the paper tubes were 3.6 mm inside diameter instead of 2.5 mm inside diameter.

Each Treatment involved six sets having six embryos per set. In Treatments (2)–(4), the resulting capsules were placed on their sides on nutrient agar surfaces in sterile covered Petri plates and incubated under continuous light for 35 days at 23° C. Data are tabulated in Table IV.

TABLE IV

| Treatment | % Normal Germinants | % Trapped Cotyledons (All) | % Trapped But Normal Cotyledons |
|---|---|---|---|
| 1 (Control) | 91% | — | — |
| 2 | 86% | 92% | 85% |
| 3 | 20% | 87% | 19% |
| 4 | 33% | 75% | 16% |

After germination, observations and conclusions were summarized as follows:

(a) The bare-embryo control (Treatment (1)) and the "shelf" capsule (Treatment (2)) produced nearly the same numbers of normal germinants; Treatments (3) and (4) involving embryos encased in paper tubes yielded lower numbers of normal germinants. This may indicate that contact with a hydrated gel is more conducive to normal embryo development than contact with paper. It is likely that using thinner paper tubes would yield higher numbers of normal germinants.

(b) In Treatments (2) to (4) involving encapsulation of the embryos, the cotyledons of a large percentage of germinants remained in the capsule after five weeks' incubation. This did not adversely affect normalcy in Treatment (2), but did in Treatments (3) and (4).

(c) Hypocotyl elongation was greatest in Treatments (1) and (2), followed by Treatment (4), then Treatment (3), indicating that the 2.5 mm diameter paper tubes were too confining for the embryos. Radical elongation was best in the controls (Treatment (1)), followed by the "shelf capsule" of Treatment (2).

(d) The 4-mm "shelf capsule" (Treatment (2)) appears to be an effective encapsulation method offering good embryo development, probably due to adequate exposure to oxygen.

EXAMPLE 6

In this Example, embryos were encapsulated in various gel formulations comprising alginate and an emulsion of a perfluorocarbon to determine the effects of such formulations on embryo germination and normal development.

A 30% emulsion of the perfluorocarbon FC-77 (perfluorobutyltetrahydrofuran, 3M Co., St. Paul, Minn.) was prepared by adding to the FC-77 a sterile surfactant, Pluronic F-68 (1.5% w/v relative to the FC-77), with the balance of the liquid being water. Pluronic F-68 is a polyoxypropylene polyoxyethylene polymer produced by BASF Corp., Parsippany, N.J. The mixture was emulsified using a Polytron homogenizer (Brinkman Instruments Model #10 20 35D, generator #PT-DA 3020/2TM) set to "High" for 30 seconds. Various amounts of the resulting emulsion were added to discrete concentrations of alginate in nutrient liquid. The purpose of using various concentrations of nutrient liquid was to provide various degrees of compensation for the dilution caused by adding the liquid to the FC-77 emulsion. Mix ratios and concentrations are as follows:

Treatment (1): Standard concentration of nutrient liquid containing alginate.

Treatment (2): A 1:1 v/v mixture of the 30% FC-77 emulsion with 2×-concentrated nutrient liquid containing alginate.

Treatment (3) A 2:1 v/v mixture of the 30% FC-77 emulsion and 3×-concentrated nutrient liquid containing alginate.

Treatment (4): A 3:1 v/v mixture of the 30% FC-77 emulsion and 4×-concentrated nutrient liquid containing alginate.

Treatment (5): A 4:1 v/v mixture of the 30% FC-77 emulsion and 5×-concentrated nutrient liquid containing alginate.

Treatment (6): "Control"; bare embryo placed on 1×-concentrated nutrient liquid containing agar.

For Treatments (1)–(5), the mixtures of emulsion and nutrient liquid with alginate were transferred immediately after preparation to a sterile gas-washing bottle and oxygenated using sterile oxygen passing therethrough for 30 minutes. The oxygenated mixtures were then placed individually in a separator funnel. Embryos were encapsulated in a manner similar to that disclosed in EPA '141 using 100 mM $Ca(NO_3)_2$ for complexing and nutrient liquid for rinsing. After encapsulation, the capsules were placed on the surface of nutrient agar in covered Petri plates. For each Treatment, three plates were prepared, each containing six embryos. All Treatments were incubated in continuous light at room temperature. A preliminary normalcy evaluation was made after two weeks' incubation and a final evaluation conducted after five weeks.

The data are tabulated in Table V and further illustrated in FIGS. 9A–9F.

TABLE V

| Treatment | 2 Week % Normal Germinants | 2 Week % Growing Thru Capsule | 5 Week % Normal Germinants | 5 Week % Growing Thru Capsule |
|---|---|---|---|---|
| 1 | 6% | 34% | 0% | 17% |
| 2 | 0% | 28% | 12% | 89% |
| 3 | 0% | 61% | 0% | 67% |
| 4 | 12% | 56% | 28% | 50% |
| 5 | 6% | 62% | 23% | 78% |
| 6 (Control) | 84% | — | 88% | — |

Figure 9A:
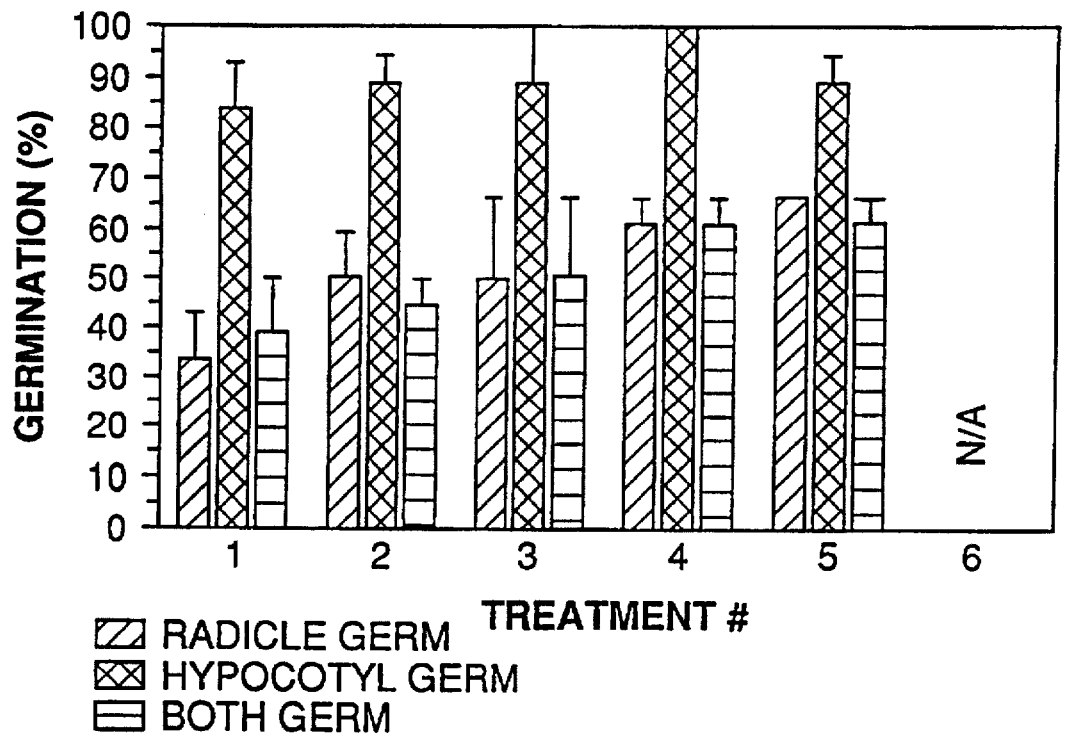
FIG. 9A is a bar graph showing the percent germination of radicles and hypocotyls from analogs of botanic seed, as evaluated after two weeks' incubation in Example 6.

Results and conclusions are summarized as follows:

(a) As shown in Table V, the presence of oxygenated perfluorocarbons in the form of an emulsion in an encapsulating hydrated gel aids germination and development of plant embryos from the alginate capsule, especially after five weeks. This is particularly evidenced by the fact that a large percentage of radicles were observed to elongate after germination in capsules containing perfluorocarbons, as shown in FIGS. 9A and 9D.

Figure 9B:
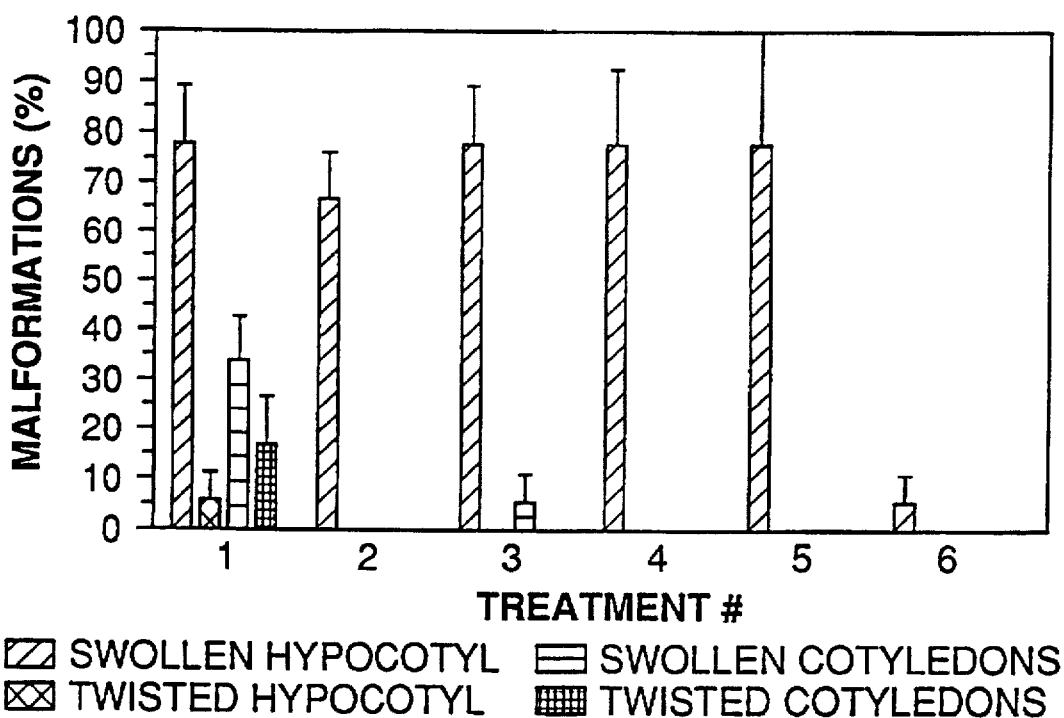
FIG. 9B is a bar graph showing percent malformations observed in germinating embryos after two weeks' incubation in Example 6.
Figure 9C:
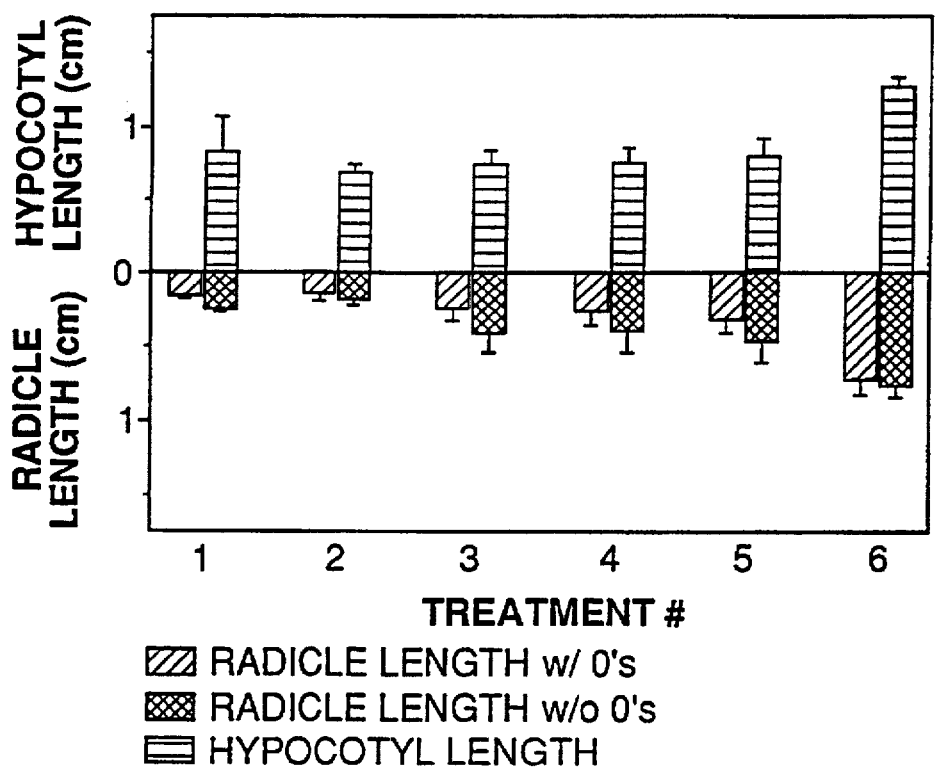
FIG. 9C is a bar graph obtained after two weeks' incubation showing lengths of radicles and hypocotyls of germinating embryos as evaluated in Example 6.
Figure 9D:
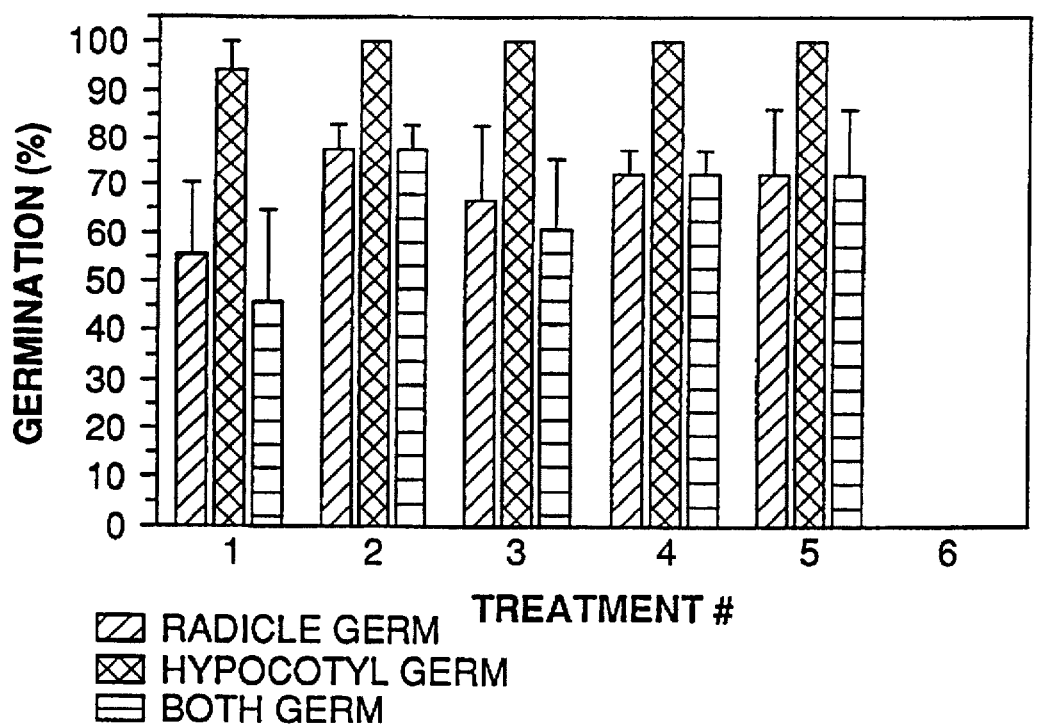
FIG. 9D is a bar graph similar to that of FIG. 9A except that the data were obtained in Example 6 after five weeks' incubation.
Figure 9E:
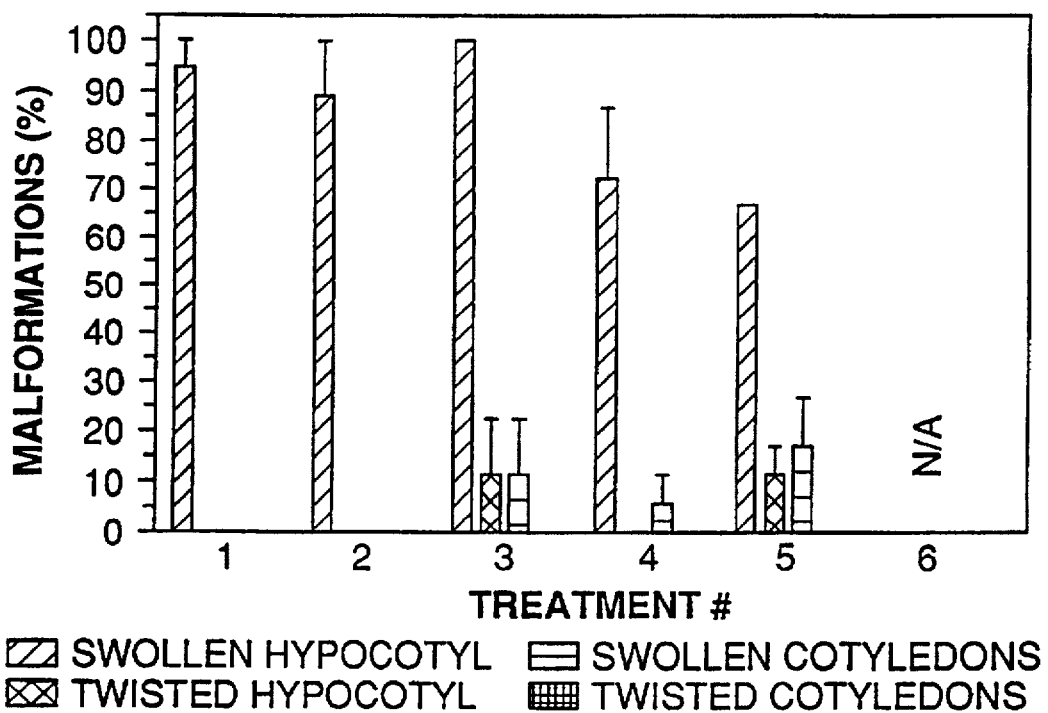
FIG. 9E is a bar graph similar to that of FIG. 9B except that the data were obtained in Example 6 after five weeks' incubation.

(b) The percentage of swollen hypocotyls was approximately the same for Treatments (1)–(5) after two weeks' incubation, as shown in FIG. 9B. However, after five weeks' incubation, higher FC-77 emulsion concentrations yielded fewer swollen hypocotyls, as shown in FIG. 9E. Since higher emulsion concentrations had correspondingly greater oxygen-absorbing ability, it appears that embryos encapsulated in gels having a higher emulsion concentrations developed more normally because they received more oxygen.

Figure 9F:
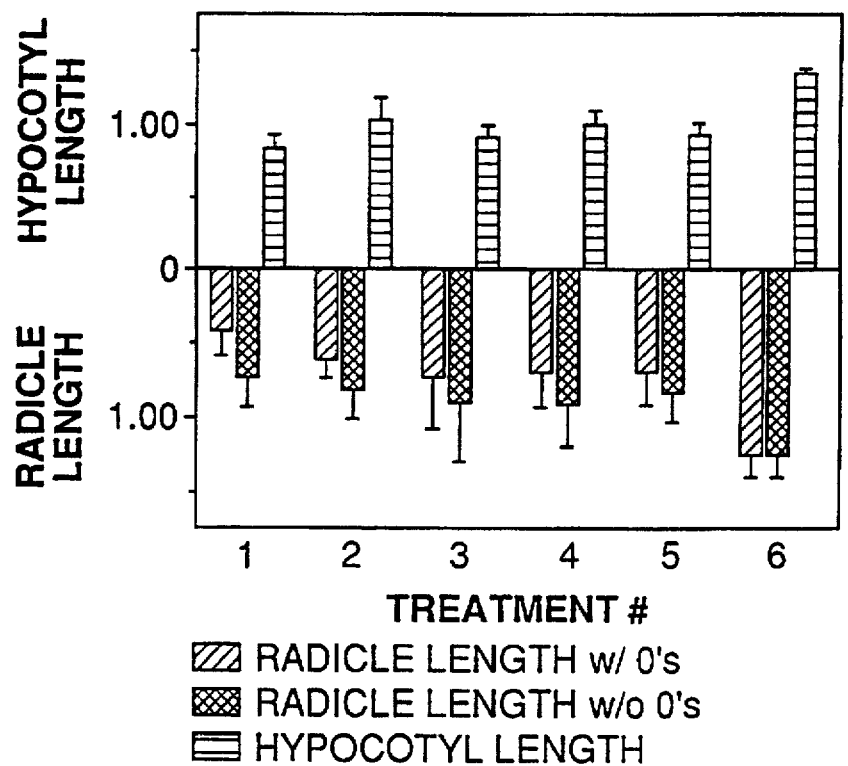
FIG. 9F is a bar graph similar to that of FIG. 9C except that the data were obtained in Example 6 after five weeks' incubation.

(c) The Controls (Treatment (6)) exhibited the best elongation of hypocotyls. All encapsulated Treatments ((1)–(5)) exhibited almost equal elongation after both two weeks' and five weeks' incubation (FIG. 9C and 9F). The fact that increasing the concentration of FC-77 had no substantial effect on hypocotyl length was not unexpected since previous studies had shown that oxygen is not as limiting for hypocotyl elongation as for radical elongation. A better indicator of low oxygen in hypocotyls is swelling.

(d) After two weeks' incubation, the Control embryos (Treatment (6)) had the longest mean radical length, as shown in FIG. 9C. Treatments (1)–(5) had somewhat variable radical lengths. After five weeks, mean radical length in the Control was still the longest, but mean lengths in Treatments (1)–(5) were substantially equal to each other, as shown in FIG. 9F. The better growth of radicles after two weeks in Treatments containing higher amounts of FC-77 correlates with the importance of the oxygen supply for radical growth. The substantially equal growth of radicles in Treatments (3)–(5) indicates that there is a concentration of oxygen in a hydrated gel above which further improvement in radical growth is not observed. However, as shown in the five week data of FIG. 9F, radical growth is not permanently inhibited at lower oxygen levels. Once the radical grows out of an oxygen-limiting environment (i.e., the gel capsule), growth appears to accelerate.

(e) As shown in FIG. 9A, the percent of germinating radicles at two weeks' incubation increased as the PFC concentration in the encapsulating gel was increased. After five weeks, the pattern changed, as shown in FIG. 9D. This indicates that more oxygen is preferred at the onset for germination when cells are beginning to rapidly divide and elongate.

(f) The data pertaining to embryos that grew through the capsules (Table V) illustrates that it would be preferable to physically restrain the cotyledons during germination. Such restraint keeps the burst capsule in contact for a time with the cotyledons rather than the hypocotyl (see FIG. 4). The cotyledons, in turn, would carry the capsule upward out of the soil in a manner similar to the way a ruptured seed coat is carried out of the soil. Then, when the cotyledons open, the capsule is discarded. The 4 mm-diameter shelf capsule tested as herein described in Example 5 is one example of a way to provide such restraint. As referred to herein, embryos that grew through the capsules are those that, as they elongated, burst through both ends of the capsule, leaving the capsule suspended around the hypocotyl (see FIG. 4). This condition can lead to swollen hypocotyls. However, there is no evidence that swollen hypocotyls decrease overall seedling survival.

(g) While there is no set pattern of normalcy in the encapsulated Treatments tested in this Example, it appears that higher concentrations of PFC yield more normal-appearing seedlings by supplying more oxygen to the germinating embryo.

EXAMPLE 7

This Example was an evaluation of the ability of an alginate capsule containing a emulsion of PFC to support germination of embryos from various species of conifers. The capsule material was prepared as two separate components that were combined to form the hydrated gel.

To prepare the alginate component, 333 mL of a 4.5% solution of Protanal LF-60 alginate (Protan, Inc.) with conventional nutrients was prepared. The pH was adjusted to 5.7, and the solution was autoclaved for 20 minutes.

The perfluorocarbon emulsion component was prepared as an emulsion of 30% FC-77 and 1.5% Pluronic F-68, made as follows: approximately 200 mL of FC-77 and 70 mL of a 0.643% w/v Pluronic F-68 solution were each autoclaved separately. After autoclaving, 30 mL of FC-77 was combined with the 70 mL of F-68 solution under sterile conditions and emulsified using a Polytron homogenizer on the "High" setting for 30 seconds. To 80 mL of the resulting emulsion were added 20 mL of the alginate component, yielding a final alginate concentration of 0.9%. The mixture was placed on a stir plate until a homogenous mixture was obtained. The resulting gel suspension was then transferred to a sterile gas-washing bottle and oxygenated under sterile conditions for 30 minutes.

To produce capsules around plant embryos, the oxygenated gel suspension was transferred to a sterile separator funnel. The stopcock n the separator funnel was adjusted to form drops in a slow stepwise manner. Whenever a drop of the gel suspension formed at the tip of the separator funnel, a plant embryo was inserted into the drop using sterile forceps, with the cotyledons pointing upward. The embryo was fully immersed within the drop. The drop was then placed in a solution of 100 mM Ca(NO$_3$)$_2$ with nutrients. This solution, termed a "complexing solution," was adjusted to pH 5.7 and autoclaved prior to use. The capsules were allowed to harden in the calcium nitrate solution for 20 minutes. Then, the calcium nitrate solution was discarded and the capsules rinsed for five minutes with nutrient liquid before placement of the resulting capsules on the surface of nutrient agar in sterile covered Petri plates.

Alginate solution lacking the PFC emulsion was prepared by combining one liter of nutrient liquid with 15 g of Protanal LF-60 alginate. After autoclaving, the gel solution was oxygenated using a gas-washing bottle as described above (if required) and transferred to a sterile separator funnel. Plant embryos were encapsulated in the alginate as described above.

Sixteen different combinations of embryo species and capsule formulations were evaluated. The Treatments were as follows:

Treatment (1): "Control" wherein Norway Spruce bare embryos were placed on the surface of nutrient agar.

Treatment (2): Norway Spruce embryos encapsulated in non-oxygenated alginate lacking PFC.

Treatment (3): Norway Spruce embryos encapsulated in oxygenated alginate lacking PFC.

Treatment (4): Norway Spruce embryos encapsulated in oxygenated PFC-containing alginate.

Treatment (5): "Control" wherein Douglas Fir bare embryos were placed on the surface of nutrient agar.

Treatment (6): Douglas Pit embryos encapsulated in non-oxygenated alginate lacking PFC.

Treatment (7): Douglas Fir embryos encapsulated in oxygenated alginate lacking PFC.

Treatment (8): Douglas Fir embryos encapsulated in oxygenated PFC-containing alginate.

Treatment (9): "Control" wherein Loblolly Pine bare embryos were placed on the surface of nutrient agar.

Treatment (10): Loblolly Pine embryos encapsulated in non-oxygenated alginate lacking PFC.

Treatment (11): Loblolly Pine embryos encapsulated in oxygenated alginate lacking PFC.

Treatment (12): Loblolly Pine embryos encapsulated in oxygenated PFC-containing alginate.

Treatment (13): "Control" wherein Norway Spruce bare somatic embryos were placed on the surface of nutrient agar.

Treatment (14): Norway Spruce somatic embryos encapsulated in non-oxygenated alginate lacking PFC.

Treatment (15): Norway Spruce somatic embryos encapsulated in oxygenated alginate lacking PFC.

Treatment (16): Norway Spruce somatic embryos encapsulated in oxygenated PFC-containing alginate.

All Treatments were incubated in continuous light at room temperature for five weeks, at which time they were examined for germination and seedling development. The data are shown in Table VI and in FIGS. 10A and 10B.

TABLE VI

| Treatment | % Normal Germinants | % That Grew Thru Capsule | % Radicle Germination | % Hypocotyl Germination | % Germination Hyp. & Rad. |
|---|---|---|---|---|---|
| 1 (Control) | 92% | — | — | — | — |
| 2 | 7% | 28% | 17% | 92% | 17% |
| 3 | 17% | 37% | 45% | 97% | 45% |
| 4 | 46% | 87% | 87% | 100% | 87% |
| 5 (Control) | 88% | — | — | — | — |
| 6 | 3% | 24% | 21% | 100% | 21% |
| 7 | 9% | 24% | 56% | 94% | 56% |
| 8 | 30% | 55% | 59% | 92% | 59% |
| 9 (Control) | 92% | — | — | — | — |
| 10 | 9% | 37% | 40% | 95% | 40% |
| 11 | 3% | 12% | 15% | 54% | 15% |
| 12 | 32% | 70% | 71% | 98% | 71% |
| 13 (Control) | 32% | — | — | — | — |
| 14 | 3% | 28% | 30% | 100% | 30% |
| 15 | 10% | 34% | 35% | 100% | 35% |
| 16 | 21% | 42% | 47% | 100% | 47% |

The results can be summarized as follows:

(a) As shown in Table VI, the oxygenated PFC-containing alginate capsule improved germination and normalcy of all species tested, particularly over germination and normalcy observed with capsules not containing any PFC.

(b) For all species except Loblolly Pine, oxygenated alginate capsules lacking PFC effected a higher number of normal germinants than non-oxygenated capsules lacking PFC, as shown in Table VI.

(c) As shown in Table VI, the number of embryos that grew through both ends of the capsule was greater with oxygenated PFC-containing alginate capsules than with the other types of capsules. This is an indication that the embryos germinating from oxygenated PFC-containing alginate capsules had a high degree of vigor since the growing embryos were strong enough to burst through both ends of the capsules. There is no evidence that this type of growth behavior is detrimental to the embryo.

(d) As shown in Table VI, hypocotyl germination was high in all Treatments (except with Loblolly Pine embryos) encapsulated in oxygenated alginate capsules lacking PFC. Radical germination was best with oxygenated PFC-containing alginate encapsulated embryos for all species tested.

(e) As shown in FIG. 10A, swollen hypocotyls were still the most prevalent abnormality, but swelling occurred less often with embryos encapsulated in oxygenated PFC-containing alginate.

(f) As shown in FIG. 10B, hypocotyl lengths increased as oxygen availability in the capsule increased. This is indicated by the fact that the oxygenated PFC containing alginate capsules yielded the longest hypocotyl lengths. Radical lengths were greatest with embryos encapsulated in oxygenated PFC-containing alginate capsules, even surpassing radical lengths of bare embryos of Loblolly Pine.

EXAMPLE 8

In this Example, several candidate surfactants for use in making an emulsion of the perfluorocarbon were evaluated.

The methods used in this Example were substantially the same as used in Example 7 except that other surfactants and surfactant concentrations were used. The study comprised six Treatments, as follows:

Treatment (1): PFC emulsion prepared using 1.5% Pluronic F-68 as a surfactant; Norway Spruce embryos encapsulated in oxygenated PFC-containing alginate.

Treatment (2): PFC emulsion prepared using 4.0% egg albumin as a surfactant; Norway Spruce embryos encapsulated in oxygenated PFC-containing alginate.

Treatment (3): PFC emulsion prepared using 1.5% sodium dodecyl sulfate as a surfactant; Norway Spruce embryos encapsulated in oxygenated PFC-containing alginate.

Treatment (4): Norway Spruce embryos encapsulated in oxygenated alginate lacking the PFC emulsion.

Treatment (5): Norway Spruce embryos encapsulated in non-oxygenated alginate lacking the PFC emulsion.

Treatment (6): "Control" wherein Norway Spruce bare embryos were placed on the surface of nutrient agar.

All Treatments utilized Norway Spruce zygotic embryos and each consisted of six encapsulated embryos prepared per covered Petri plate, six plates for each Treatment. All plates Were incubated in continuous light at room temperature for five weeks, at which time the germinants were evaluated for germination success and other parameters. The results are shown in Table VII and in FIGS. 11A and 11B.

TABLE VII

| Treatment | % Normal Germinants | % Growth Thru Capsule | % Radicle Germination | % Hypocotyl Germination | % Germination Hyp. & Rad. |
|---|---|---|---|---|---|
| 1 | 56% | 94% | 94% | 100% | 94% |
| 2 | 70% | 86% | 86% | 97% | 86% |
| 3 | 0% | 0% | 0% | 0% | 0% |
| 4 | 15% | 57% | 59% | 100% | 59% |
| 5 | 24% | 35% | 41% | 89% | 35% |
| 6 (Control) | 100% | — | — | — | — |

Conclusions drawn from the results can be summarized as follows:

(a) As shown in Table VII, Treatment (3), sodium dodecyl sulfate is not an effective surfactant in that it caused mortality of all embryos in contact with it.

(b) As shown in Table VII, Treatments (2) and (1), respectively, egg albumin and Pluronic F-68 are both effective surfactants for PFCs such as FC-77. Egg albumin produced more normal germinants, but Pluronic F-68 yielded more germinated embryos.

Figure 11A:
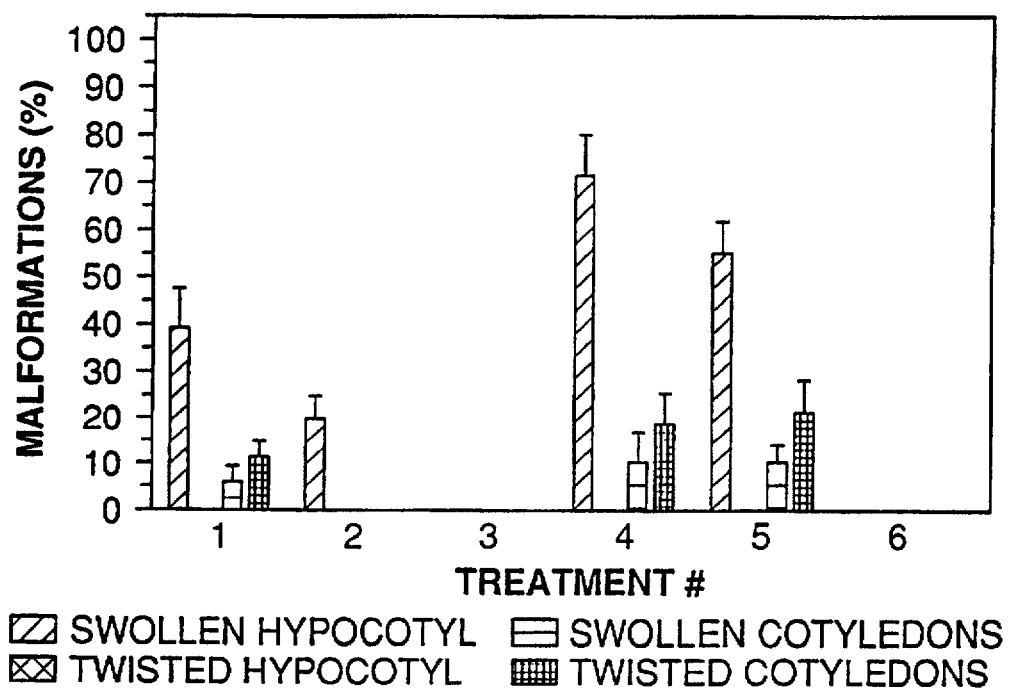
FIG. 11A is a bar graph showing percent malformations observed in embryos, as evaluated in Example 8.
Figure 11B:
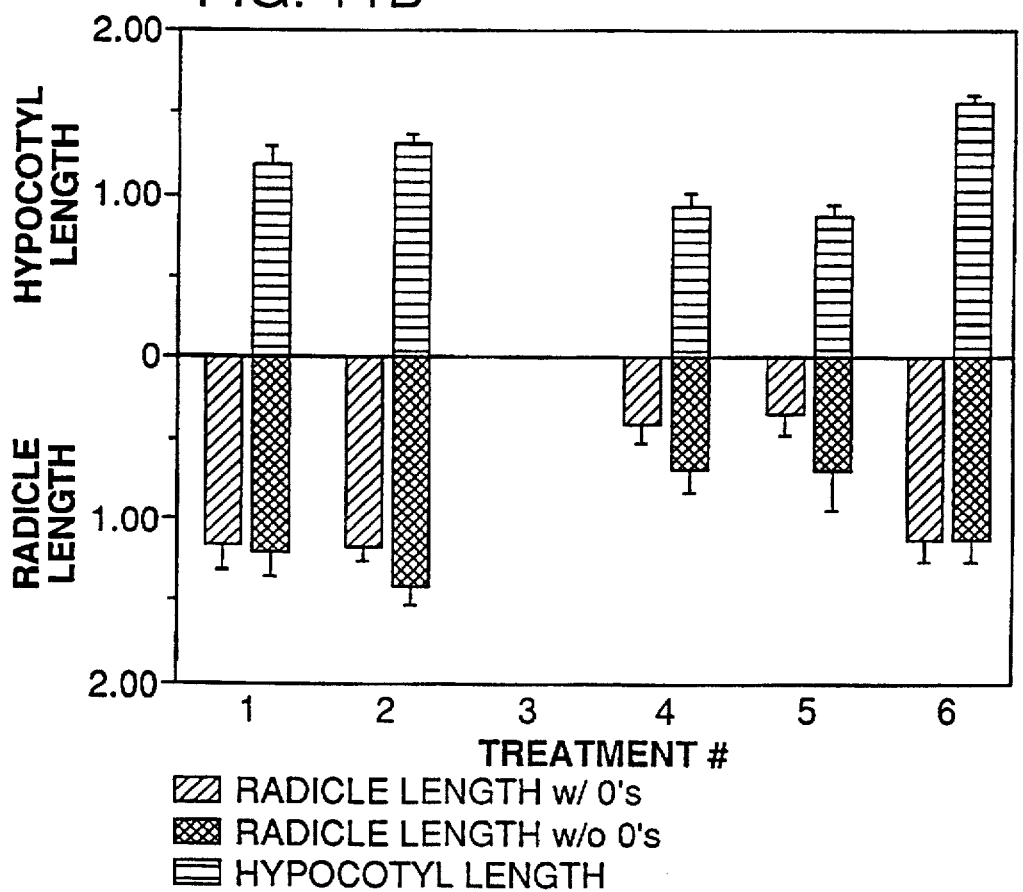
FIG. 11B is a bar graph showing lengths of radicles and hypocotyls of the germinating embryos evaluated in Example 8.

(c) As shown in Table VII and FIG. 11A, oxygenated PFC-containing alginate capsules yielded a higher level of normalcy and a higher total number of germinants than seen with alginate capsules lacking PFC, whether oxygenated or not.

(d) As expected, bare embryos grown on agar produced the most normal germinants.

(e) Treatment (1) yielded the most embryos that grew through the capsule (Table VII).

EXAMPLE 9

In this Example, the ability of various perfluorocarbons to supply oxygen to encapsulated embryos was evaluated.

The methods employed in this Example are the same as those in Example 7 except that several different perfluorocarbons were used. The various Treatments tested were as follows:

Treatment (1): Norway Spruce embryos encapsulated in oxygenated alginate containing an emulsion of 30% FC-77 plus 1.5% Pluronic F-66.

Treatment (2): Norway Spruce embryos encapsulated in oxygenated alginate containing an emulsion of 30% perfluorodecalin (another type of PFC) and 1.5% Pluronic F-68.

Treatment (3): Norway Spruce embryos encapsulated in oxygenated alginate containing an emulsion of 30% perfluorotributylamine (another type of PFC) and 1.5% Pluronic F-66.

Treatment (4): Norway Spruce embryos encapsulated in oxygenated alginate lacking PFC.

Treatment (5): Norway Spruce embryos encapsulated in non-oxygenated alginate lacking PFC.

Treatment (6): "Control" wherein Norway Spruce bare embryos were placed on the surface of nutrient agar.

All Treatments utilized Norway Spruce zygotic embryos and each consisted of six covered Petri plates containing six encapsulated embryos per plate. Treatments were incubated in continuous light at room temperature for five weeks, after which germination success and other parameters were evaluated. Results are tabulated in Table VIII and shown in FIGS. 12A and 12B.

TABLE VIII

| Treatment | % Normal Germinants | % Growth Thru Capsule | % Radicle Germination | % Hypocotyl Germination | % Germination Hyp. & Rad. |
|---|---|---|---|---|---|
| 1 | 69% | 92% | 95% | 100% | 97% |
| 2 | 35% | 70% | 77% | 100% | 77% |
| 3 | 61% | 81% | 86% | 100% | 86% |
| 4 | 34% | 56% | 56% | 100% | 56% |
| 5 | 29% | 60% | 65% | 100% | 65% |
| 6 (Control) | 97% | — | — | — | — |

The conclusions can be summarized as follows:

(a) As shown in Table VIII, it appears that perfluorodecalin (Treatment (2)) does not produce as many normal germinants as does FC-77 (Treatment (1)) and perfluorotributylamine (Treatment (3)). However, perfluorodecalin produces substantially the same number of normal germinants as oxygenated alginate lacking PFC (Treatment (4)). This could be due to a short half life of the perfluorodecalin emulsion.

(b) It appears that FC-77 is the preferred perfluorocarbon among those tested in this Example for use in analogs of botanical seed, at least of conifers.

(c) As expected, bare embryos (Treatment (6)) had the highest percentage of normal germinants, as shown in Table VIII. Treatment (5), involving a non-oxygenated alginate capsule, had the lowest percent of normal germinants.

(d) Treatment (1) had the highest percent of embryos growing through the capsule (Table VIII).

(e) All hypocotyl in all Treatments germinated (Table VIII). The percentages of radical germination and germination of both radical and hypocotyl were highest in Treatments having perfluorocarbon emulsions in the alginate, as shown in Table VIII.

Figure 12A:
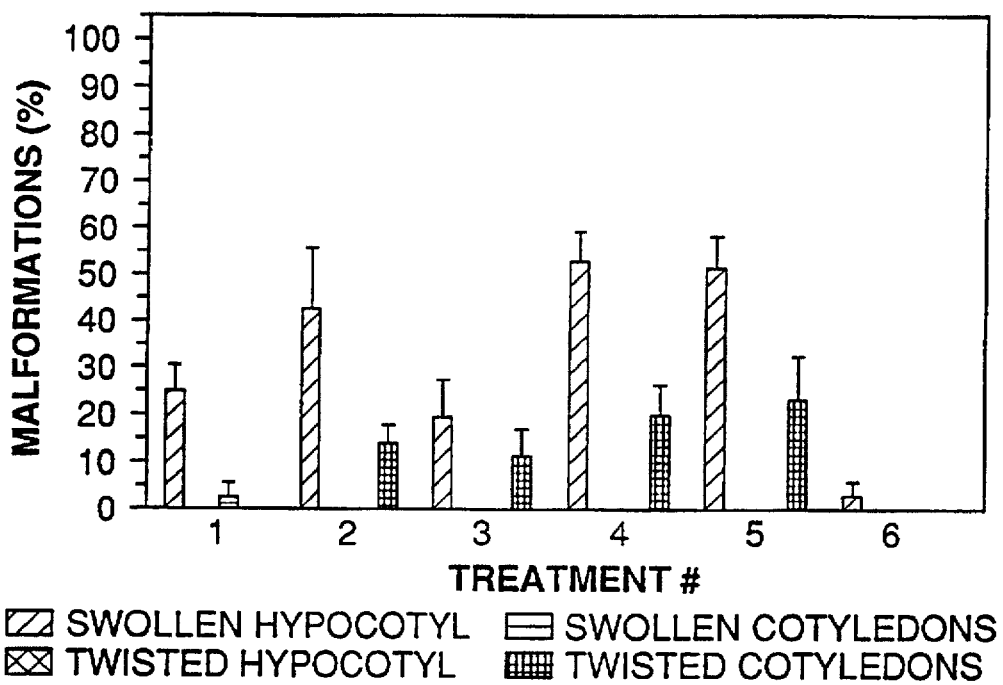
FIG. 12A is a bar graph showing percent malformations observed in embryos, as evaluated in Example 9.

(f) As shown in FIG. 12A, Treatments (2), (4), and (5) yielded approximately two times more abnormalities than the other three Treatments, where swollen hypocotyl were the most prevalent abnormality.

Figure 12B:
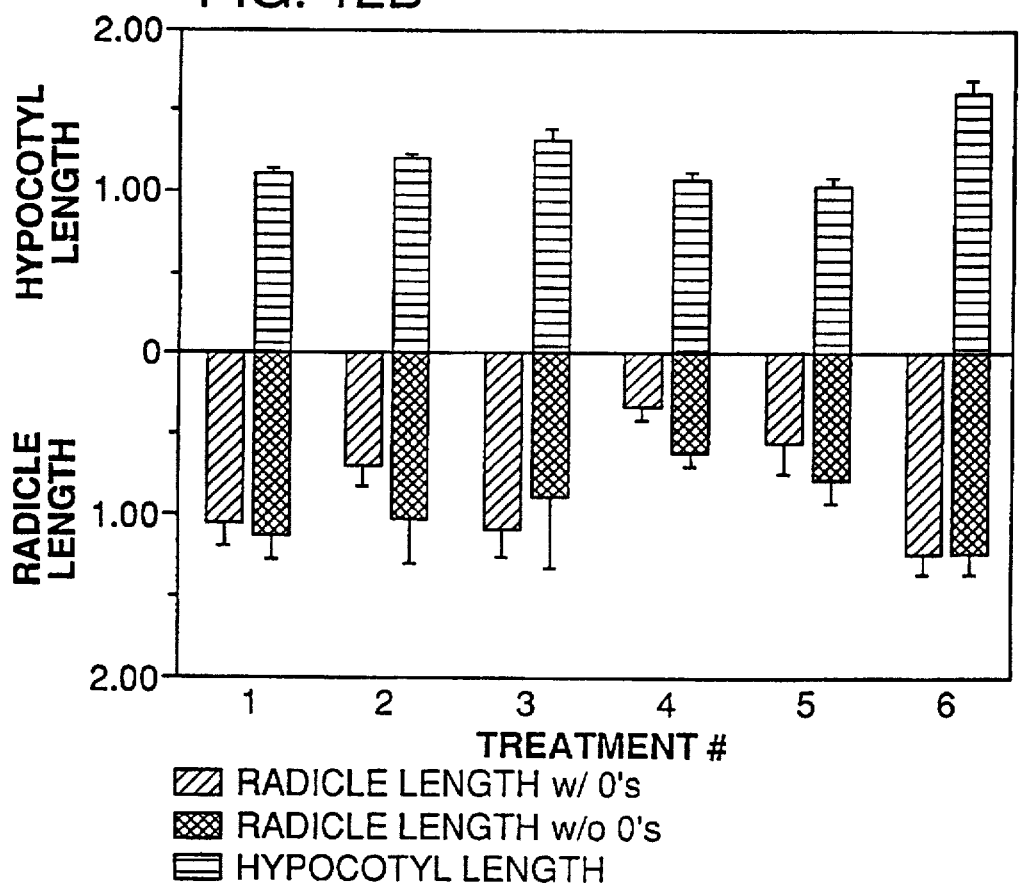
FIG. 12B is a bar graph of lengths of radicles and hypocotyls observed in the germinating embryos of Example 9.

(g) Of the encapsulated embryos, radical lengths and hypocotyl lengths were longest when embryos germinated from oxygenated PFC-containing gel capsules (FIG. 12B).

EXAMPLE 10

The objective in this Example was two-fold: (1) to evaluate the effect on normal germination of an alginate capsule containing only surfactant and no PFC; and (2) to evaluate the effect on normal germination of encapsulating embryos in non-oxygenated PFC-containing alginate capsules.

The methods used for encapsulating embryos are as described above in Example 7. Individual sets of Norway Spruce embryos were subjected to one of the following Treatments:

Treatment (1): Embryos encapsulated in oxygenated alginate containing FC-77 emulsion, according to Example 7.

Treatment (2): Embryos encapsulated in non-oxygenated alginate containing FC-77 emulsion.

Treatment (3): Embryos encapsulated in oxygenated alginate lacking PFC but containing 1.5% Pluronic F-68.

Treatment (4): Embryos encapsulated in non-oxygenated alginate lacking PFC but containing 1.5% Pluronic F-68.

Treatment (5): Embryos encapsulated in non-oxygenated alginate lacking both PFC and surfactant.

Treatment (6): Embryos encapsulated in oxygenated alginate lacking both PFC and surfactant.

Treatment (7): "Control" wherein bare embryos were grown on the surface of nutrient agar.

The concentration of Pluronic F-66 in the alginate capsules used in Treatments (3) and (4) was the same as used in Treatments (1) and (2). Each Treatment comprised six covered Petri dishes, each containing six embryos. All Treatments were incubated in continuous light at room temperature for 35 days. Results are shown in Table IX and FIGS. 13A and 13B.

TABLE IX

| Treatment | % Normal Germinants | % Growth Thru Capsule | % Radicle Germination | % Hypocotyl Germination | % Germination Hyp. & Rad. |
|---|---|---|---|---|---|
| 1 | 35% | 82% | 82% | 100% | 82% |
| 2 | 27% | 52% | 49% | 100% | 49% |
| 3 | 18% | 36% | 36% | 97% | 36% |
| 4 | 6% | 19% | 20% | 95% | 20% |
| 5 | 9% | 28% | 28% | 100% | 28% |
| 6 | 6% | 34% | 34% | 100% | 34% |
| 7 (Control) | 94% | — | — | — | — |

The results and conclusions can be summarized as follows:

(a) As shown in Table IX, both oxygenated and non-oxygenated PFC-containing alginate capsules (Treatments (1) and (2)) yielded more germinants and a higher percent of normal germinant than non-PFC containing alginate capsules.

(b) As shown n Table IX, Pluronic F-68, in an alginate capsule lacking PFC, appears to increase germination when the capsule has been oxygenated (Treatment (3)), and to decrease germination when the capsule is non-oxygenated (Treatment (4)).

(c) Of the capsule formulations tested, the oxygenated alginate capsule containing PFC emulsion appears to be the best.

(d) It appears that the benefit of adding an emulsion of PFC to the alginate capsule is derived from the presence of the PFC and not merely the surfactant therein.

(e) Treatment (1) exhibited the highest percent of embryos that grew through the capsule (Table IX).

(f) Hypocotyl germination was high with all Treatments (Table IX). Treatment (1) exhibited the highest values of percent germination of both radical and hypocotyl.

Figure 13A:
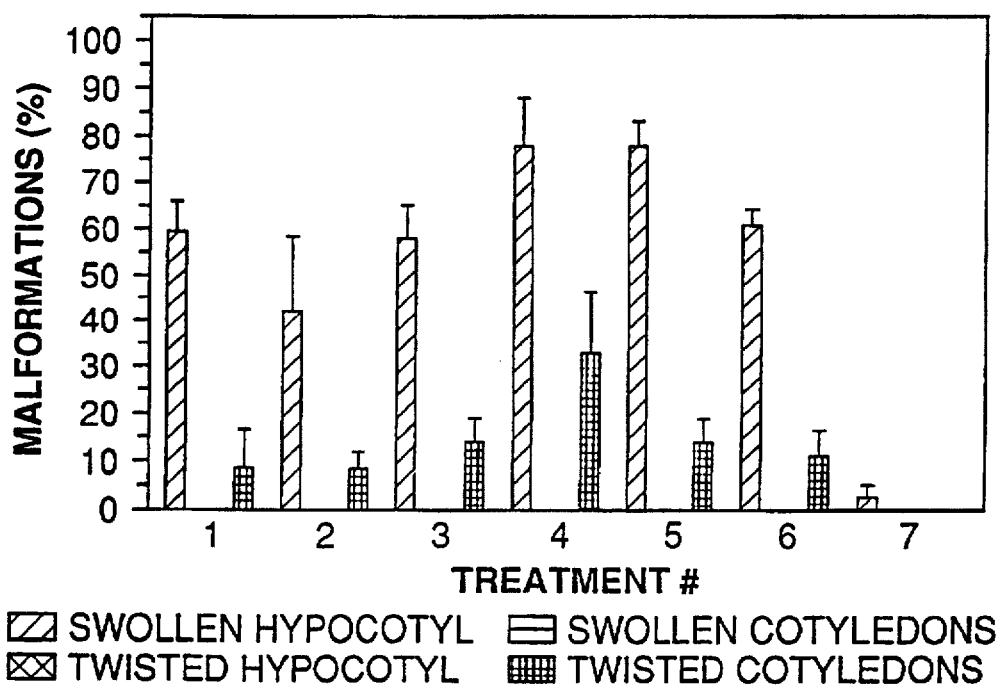
FIG. 13A is a bar graph of percent malformations observed in embryos germinating from capsules as described in Example 10.

(g) The only types of malformations observed were swollen hypocotyl and twisted cotyledons (FIG. 13A).

Figure 13B:
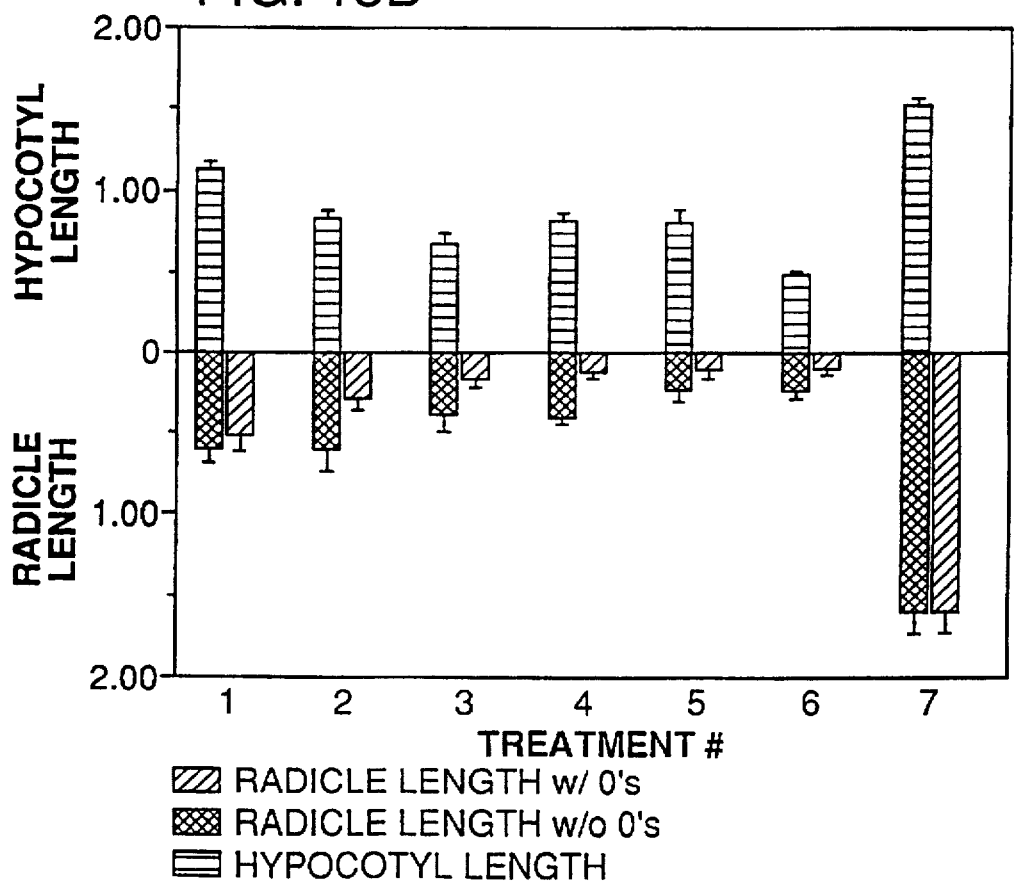
FIG. 13B is a bar graph of lengths of radicles and hypocotyls observed in the germinating embryos of Example 10.

(h) The controls (Treatment (7)) exhibited the longest radicles and hypocotyl (FIG. 13B). Treatment (1) embryos exhibited the longest hypocotyl lengths of the encapsulated embryos, as well as the longest radical lengths.

EXAMPLE 11 six experimental treatments were performed to compare alginate gels with agar gels. The seed analog embodiment that was tested comprised a cylinder of the gelled material having a diameter of about 6 mm and a length of about 8 mm. A core portion about 6 mm long and 1.5 mm in diameter, located along the longitudinal axis of the cylinder, was removed from one end of the cylinder to create a cavity for the embryo. An embryo was inserted into each cavity, cotyledon-end first. Douglas-fir zygotic embryos were used in all tests in the example. A standard procedure of six replications with six embryos per replicate was followed.

The alginate cylinders were made as follows. First, two concentrated (5x) gel solutions were prepared. One of the concentrated gel solutions comprised 4.5% sodium alginate; the other comprised 6.0%. Each concentrated gel solution was similar in composition to sodium alginate solutions used in earlier examples. Each concentrated gel solution was degassed under vacuum for 14 to 16 hours, then autoclaved. A perfluorocarbon (FC-77) and a 1.5% w/v water solution of nonionic surfactant (Pluronic F-68) were autoclaved separately. After autoclaving, 30 mL of the perfluorocarbon and 70 mL of the surfactant solution were combined and emulsified under sterile conditions. Then, 80 mL of the resulting emulsion was combined with 20 mL of the concentrated gel solution, yielding a 0.9% and 1.2% solution, respectively, of "gel medium" (alginate artificial gametophyte). The gel media were poured into separate filter-paper cylinders 6 mm in diameter previously saturated with 100 mM CaNO$_3$ solution. The filled cylinders were placed in a 200 mM CaNO$_3$ solution for 15 minutes. The filter paper was removed and the resulting alginate gel cylinders were treated for another 45 minutes in 100 mM CaNO$_3$ to ensure complete ion exchange. The axial core portions were then removed as described above for later insertion of the embryos in the resulting cavities.

The agar cylinders were made as follows. First, three concentrated (5x) agar solutions were prepared: 8.0%, 9.0%, and 10% agar. Each concentrated solution was autoclaved and, while still hot, placed in a 50° C. water bath. A perfluorocarbon emulsion was made as described above and mixed with the still-warm concentrated agar solution in a ratio of 4 parts emulsion to 1 part concentrated gel solution, yielding a 1.6%, a 1.8%, and a 2.0% "agar medium" (agar artificial gametophyte), respectively. The agar gel media were poured into individual sterile dishes and allowed to set in a room-temperature environment. Cylinders 6 mm in diameter were cut from the gel and cored as described above to receive the embryos.

Douglas-fir zygotic embryos were dissected from seeds. One embryo was placed in each cavity of the agar and alginate cylinders to form seed analogs. The seed analogs were then oxygenated for 18 hours using the procedure as described above in connection with FIGS. 14 and 15. The seed analogs were then placed on an agar surface under a 24-hour photoperiod for germination. After 35 days the resulting germinants were examined and scored. A control, comprising bare zygotic embryos placed on an agar surface in a petri dish, showed essentially normal development of the germinants. The 0.9% and 1.2% alginate seed analogs each exhibited germination percentages of 50% and 89% of plants containing both radicles and hypocotyl, respectively. However, these germinants exhibited only 14% and 17% normalcy, respectively. The predominant abnormalities were swollen hypocotyl and swollen cotyledons. Seed analogs containing 1.6%, 1.8%, and 2.0% agar exhibited germination percentages of 89%, 63% and 75%, respectively. These germinants exhibited 25%, 17%, and 25% normalcy, respectively. As with the alginate seed analogs, abnormalities were predominantly swollen hypocotyl and cotyledons. A high percentage of the germinants split the gel cylinders as they developed. This problem has been corrected in subsequent studies by the use of a rigid outer shell around the gel mass. Malformations in germinants were significantly reduced by inclusion of an outer shell.

The results of this Example indicate that, at least under the conditions of this Example, agar is at least equivalent and possibly superior to complexed alginate for use as a gel in seed analogs according to the present invention.

EXAMPLE 12

Agar media were prepared as described in Example 11, comprising 1.8% agar. The oxygen carrier was either the perfluorcarbon used in Example 11 or an equal volume of a silicone oil substituted for the perfluorocarbon. The silicone oil was "DC-200", a polydimethylsiloxane of 5 centistokes (cst) viscosity, available from Dow Corning Corp., Midland, Michigan. A number of agar media solutions were prepared each also containing an emulsifier. Four different emulsifiers were investigated, including 1.5% w/v Pluronic F-68 non-ionic surfactant, 4.0% w/v egg albumin, 4.0% w/v egg lecithin, and 0.5% w/f "DC-193", all in water. DC-193 is a polydimethylsiloxane-polyethylene oxide block copolymer also available from Dow Corning Corp. All seed analogs produced using these agar media were oxygenate as in Example 11. Sample identification is as follows:

Sample 1: Bare embryo control on agar plates.

Sample 2: Perfluorocarbon FC-77 with Pluronic F-68 emulsifier.

Sample 3: Silicone oil DC-200 with Pluronic F-68 emulsion.

Sample 4: Perfluorocarbon FC-77 with egg albumin emulsifier.

Sample 5: Silicone oil DC-200 with egg albumin emulsifier.

Sample 6: Perfluorocarbon FC-77 with egg lethicin emulsifier.

Sample 7: Silicone oil DC-200 with egg lethicin emulsifier.

Sample 8: Silicone oil DC-200 with DC-193 emulsifier.

After germination for 5 weeks on the surface of nutrient agar gel in continuous light, the following results were noted.

TABLE X

| Sample No. | % Germination | % Normalcy |
|---|---|---|
| 1 (Control) | 100 | 92 |
| 2 | 97 | 3 |
| 3 | 50 | 0 |
| 4 | 81 | 0 |
| 5 | 47 | 0 |
| 6 | 97 | 0 |
| 7 | 89 | 0 |
| 8 | 66 | 0 |

As noted previously, the most common abnormalities were swollen hypocotyl and cotyledons. These abnormalities apparently arise from either the presence of liquid in the cavity containing the embryo or the failure of the germinant to completely free its cotyledons from the artificial gametophyte.

Silicone oil appears to be an effective oxygen carrier although, under the conditions of this Example, silicone oil appears to be less advantageous than perfluorocarbon. This is believed to be due to the large particle size of the silicone emulsions compared with those of the perfluorocarbon, a problem that can be readily overcome by, for example, using higher shear forces when preparing the emulsion.

Having illustrated and described the principles of the invention in multiple embodiments and examples, it should be apparent to those skilled in the art that the invention can be modified in arrangement and detail without departing from such principles. We claim all modifications coming within the spirit and scope of the following claims.

We claim:

1. A manufactured seed comprising:
   (a) totipotent plant tissue having a shoot end; and
   (b) a restraint, enclosing at least the shoot end, that resists penetration by the shoot end during germination, permits access of the totipotent plant tissue to gases and liquids, is contacted by the shoot end substantially at onset of germination, and is shed distally off the shoot end during germination.

2. The manufactured seed of claim 1 wherein the restraint is permeable to gases and liquids.

3. The manufactured seed of claim 2 wherein the restraint is made from a porous material.

4. The manufactured seed of claim 1 further comprising a hydrated gel disposed proximate the totipotent plant tissue so as to allow liquid transfer from the gel to the plant tissue.

5. The manufactured seed of claim 4 wherein the gel at least partially surrounds the plant tissue.

6. The manufactured seed of claim 5 wherein he gel at least partially surrounds the restraint and the totipotent plant tissue.

7. The manufactured seed of claim 4 wherein the gel defines a longitudinal cavity and the restraint is disposed in the cavity so as to contact the gel.

8. The manufactured seed of claim 7 wherein the cavity has interior walls and the restraint is adjacent the interior walls of the cavity.

9. The manufactured seed of claim 7 wherein the restraint has an exterior surface substantially conforming to the cavity.

10. The manufactured seed of claim 9 wherein the restraint has an inner surface conforming to at least the shoot end of the totipotent plant tissue.

11. The manufactured seed of claim 4 wherein the gel comprises an inert chemical compound that absorbs or carries molecular oxygen.

12. The manufactured seed of claim 11 wherein the inert substance is selected from the group consisting of perfluorocarbons, silicone oils, and mixtures thereof.

13. The manufactured seed of claim 4 wherein the restraint comprises a porous sheet interposed between the totipotent plant tissue and the hydrated gel.

14. The manufactured seed of claim 1 wherein the restraint comprises a rigid porous tube having a closed end, wherein the shoot end of the totipotent plant tissue is oriented in the porous tube toward the closed end of the tube.

15. The manufactured seed of claim 1 wherein the restraint comprises a hardened hydrated gel.

16. The manufactured seed of claim 1 wherein the totipotent plant tissue is a plant embryo.

17. The manufactured seed of claim 1 wherein the shoot end comprises at least one cotyledon.

18. The manufactured seed of claim 1 wherein the restraint has a closed end and an open end, and the shoot end of the totipotent plant tissue is oriented toward the closed end.

19. An improved manufactured seed comprising a unit of totipotent plant tissue having a shoot end, the improvement comprising a restraint enclosing at least the shoot end that resists penetration by the shoot end during germination, permits access of the plant tissue to gases and liquids, is contacted by the shoot end substantially at onset of germination, and is shed distally off the shoot end during germination.

20. A manufactured seed comprising:
   (a) totipotent plant tissue having a shoot end; and
   (b) a gas- and liquid-permeable restraint having an open end and a closed end, the closed end enclosing at least the shoot end of the totipotent plant tissue such that the shoot end is oriented toward the closed end, wherein, substantially at onset of germination, the shoot end contacts the restraint without penetrating the restraint and urges the restrain to be shed distally off the shoot end during germination.

21. A manufactured seed comprising:
   (a) totipotent plant tissue having a shoot end;
   (b) a hydrated gel proximate the totipotent plant tissue; and
   (c) a restraint, situated between at least the shoot end of the totipotent plant tissue and the gel, that (i) resists penetration of the gel by the shoot end during germination, and (ii) is shed distally off the shoot end during germination.

22. The manufactured seed of claim 21 wherein the gel comprises an inert chemical compound that absorbs or carries molecular oxygen.

23. The manufactured seed of claim 21 wherein the restraint has an open end and a closed end and encloses at least the shoot end of the totipotent plant tissue such that the shoot end is oriented toward the closed end of the restraint.

24. The manufactured seed of claim 21 wherein he restraint is contacted by the shoot end substantially at onset of germination.

25. The manufactured seed of claim 21 wherein the restraint is in contact with the gel or the shoot end or both.

26. The manufactured seed of claim 21 wherein the restraint is made of a porous material.

27. A manufactured seed comprising:

(a) totipotent plant tissue having a shoot end;

(b) a hydrated gel proximate the totipotent plant tissue; and (c) a restraint, having an open end and a closed end, the closed end enclosing at least the shoot end of the totipotent plant tissue such that the shoot end is oriented toward the closed end, the restraint being operable to (i) resist penetration of the gel by the shoot end during germination, and (ii) be shed distally off the shoot end during germination.

28. A method for germinating a unit of totipotent plant tissue, the method comprising:

(a) providing a manufactured seed comprising (i) a unit of totipotent plant tissue having a shoot end and (ii) a restraint, enclosing at least the shoot end, that resists penetration by the shoot end during germination, permits access of the totipotent plant tissue to gases and liquids, is contacted by the shoot end substantially at onset of germination, and is shed distally off the shoot end during germination; and (b) incubating the manufactured seed under conditions that cause the totipotent plant tissue to germinate and produce a germinant.

29. A method of making a manufactured seed, the method comprising the steps of:

(a) providing totipotent plant tissue having a shoot (b) enclosing at least the shoot end of the totipotent plant tissue with a restraint that (i) resists penetration by the shoot end during germination, (ii) permits access of the totipotent plant tissue to gases and liquids, (iii) is contacted by the shoot end substantially at onset of germination, and (iv) is shed distally off the shoot end during germination.

30. The method of claim 29 further comprising the step of disposing the totipotent plant tissue proximate a hydrated gel so as to allow liquid transfer from the gel to the totipotent plant tissue, wherein the restraint prevents penetration of the gel by the shoot end during germination.

31. A method of making a manufactured seed comprising the steps of:

(a) providing totipotent plant tissue having a shoot end;

(b) enclosing at least the shoot end of the totipotent plant tissue with a restraint:

(c) disposing the totipotent plant tissue proximate a hydrated gel, wherein the restraint prevents penetration of the gel by the shoot end of the totipotent plant tissue upon germination of the totipotent plant tissue and permits liquid transfer from the gel to the totipotent plant tissue.

32. A method for germinating a unit of totipotent plant tissue comprising the steps of:

(a) providing a manufactured seed comprising: (i) a unit of totipotent plant tissue having a shoot end: (ii) a hydrated gel proximate the totipotent plant tissue; and (iii) a restraint, having an open end and a closed end, the closed end enclosing at least the shoot end of the totipotent plant tissue such that the shoot end is oriented toward the closed end, the restraint being operable to resist penetration of the gel by the shoot end during germination, and be shed distally off the shoot end during germination; and (b) incubating the manufactured seed under conditions that cause the totipotent plant tissue to germinate and produce a germinant.

* * * * *